(12) United States Patent
Loven et al.

(10) Patent No.: US 11,331,520 B2
(45) Date of Patent: May 17, 2022

(54) SYSTEMS AND METHODS FOR PRODUCING AND DELIVERING ULTRASONIC THERAPIES FOR WOUND TREATMENT AND HEALING

(71) Applicant: Celularity Functional Regeneration, LLC, Warren, NJ (US)

(72) Inventors: Ross Loven, Mankato, MN (US); Jeff Sampson, Minneapolis, MN (US); Li Qin, North Mankato, MN (US); Ryan Glen Tetzloff, Minnetonka, MN (US); Douglas Duchon, Chanhassen, MN (US)

(73) Assignee: SANUWAVE HEALTH, INC., Suwanee, GA (US)

( * ) Notice: Subject to any disclaimer, the term of this patent is extended or adjusted under 35 U.S.C. 154(b) by 293 days.

(21) Appl. No.: 16/599,389

(22) Filed: Oct. 11, 2019

(65) Prior Publication Data
US 2020/0179725 A1  Jun. 11, 2020

Related U.S. Application Data

(63) Continuation of application No. 14/546,808, filed on Nov. 18, 2014.

(60) Provisional application No. 61/909,086, filed on Nov. 26, 2013.

(51) Int. Cl.
*A61N 7/00* (2006.01)

(52) U.S. Cl.
CPC ........ *A61N 7/00* (2013.01); *A61N 2007/0017* (2013.01); *A61N 2007/0073* (2013.01)

(58) Field of Classification Search
CPC .............. A61N 7/00; A61N 2007/0073; A61N 2007/0017
See application file for complete search history.

(56) References Cited

U.S. PATENT DOCUMENTS

| | | | |
|---|---|---|---|
| 2,534,046 | A | 12/1950 | Mau |
| 2,889,852 | A | 6/1959 | Dunlap |
| 3,207,181 | A | 9/1965 | Willis |

(Continued)

FOREIGN PATENT DOCUMENTS

| | | |
|---|---|---|
| CA | 2421798 | 3/2002 |
| CA | 2 359 426 | 4/2002 |

(Continued)

OTHER PUBLICATIONS

U.S. Appl. No. 90/007,613, filed Sep. 25, 2000, Babaev.

(Continued)

*Primary Examiner* — Hien N Nguyen
(74) *Attorney, Agent, or Firm* — Patterson Thuente Pedersen, P.A.

(57) ABSTRACT

One embodiment is directed to a non-contact, medical ultrasound therapy system for generating and controlling low frequency ultrasound. The ultrasound therapy system includes a treatment wand including an ultrasonic transducer, a generator unit, and a cable coupling the treatment wand to the generator unit. The generator unit generates electric power output to drive the ultrasonic transducer and includes a digital frequency generator, wherein the generator unit digitally controls energy output at resonance frequency of the ultrasonic transducer.

1 Claim, 13 Drawing Sheets

(56) References Cited

U.S. PATENT DOCUMENTS

| | | |
|---|---|---|
| 3,243,122 A | 3/1966 | Snaper |
| 3,275,059 A | 9/1966 | McCullough |
| 3,392,916 A | 7/1968 | Engstrom |
| 3,433,226 A | 3/1969 | Boyd |
| 3,504,887 A | 4/1970 | Okerblom |
| 3,522,801 A | 8/1970 | Robinson |
| 3,561,444 A | 2/1971 | Boucher |
| 3,636,947 A | 1/1972 | Balamuth |
| 3,685,634 A | 8/1972 | Bergling |
| 3,685,691 A | 8/1972 | Ianelli |
| 3,685,694 A | 8/1972 | Ianelli |
| 3,765,606 A | 10/1973 | Moss |
| 3,860,173 A | 1/1975 | Sata |
| 3,874,372 A | 4/1975 | LeBon |
| 3,952,918 A | 4/1976 | Poitras |
| 4,052,004 A | 10/1977 | Martin |
| 4,085,893 A | 4/1978 | Durley |
| 4,153,201 A | 5/1979 | Berger |
| 4,185,502 A | 1/1980 | Frank |
| 4,192,294 A | 3/1980 | Vasilevsky |
| 4,251,031 A | 2/1981 | Martin |
| 4,271,705 A | 6/1981 | Crostack |
| 4,294,407 A | 10/1981 | Reichl |
| 4,301,093 A | 11/1981 | Eck |
| 4,301,968 A | 11/1981 | Berger |
| 4,309,989 A | 1/1982 | Fahim |
| 4,319,155 A | 3/1982 | Nakai |
| 4,331,137 A | 5/1982 | Sarui |
| 4,334,531 A | 6/1982 | Reichl |
| 4,352,459 A | 10/1982 | Berger |
| 4,414,202 A | 11/1983 | Anthony |
| 4,428,531 A | 1/1984 | Martin |
| 4,466,571 A | 8/1984 | Muhlbauer |
| 4,530,360 A | 7/1985 | Duarte |
| 4,541,564 A | 9/1985 | Berger |
| 4,551,139 A | 11/1985 | Plaas et al. |
| 4,582,149 A | 4/1986 | Slaughter, Jr. |
| 4,582,654 A | 4/1986 | Kamicky |
| 4,619,400 A | 10/1986 | Van Der Burgt |
| 4,642,581 A | 2/1987 | Erickson |
| 4,655,393 A | 4/1987 | Berger |
| 4,659,014 A | 4/1987 | Soth |
| 4,679,551 A | 7/1987 | Anthony |
| 4,726,523 A | 2/1988 | Kokubo |
| 4,726,525 A | 2/1988 | Yonekawa |
| 4,733,820 A | 3/1988 | Endo |
| 4,756,478 A | 7/1988 | Endo |
| 4,767,402 A | 8/1988 | Kost et al. |
| 4,783,003 A | 11/1988 | Hirabayashi |
| 4,790,479 A | 12/1988 | Matsumoto |
| 4,793,339 A | 12/1988 | Matsumoto |
| 4,815,661 A | 3/1989 | Anthony |
| 4,818,697 A | 4/1989 | Liboff |
| 4,850,534 A | 7/1989 | Takahashi et al. |
| 4,877,989 A | 10/1989 | Drews |
| 4,883,045 A | 11/1989 | Theisz |
| 4,905,671 A | 3/1990 | Senge |
| 4,930,700 A | 6/1990 | McKown |
| 4,941,614 A | 7/1990 | Ilott |
| 4,941,618 A | 7/1990 | Hildebrand |
| 4,961,885 A | 10/1990 | Avrahami |
| 4,982,730 A | 1/1991 | Lewis, Jr. |
| 5,002,059 A | 3/1991 | Crowley |
| 5,013,241 A | 5/1991 | Gutfeld |
| 5,040,537 A | 8/1991 | Katakura |
| 5,045,066 A | 9/1991 | Scheuble |
| 5,062,795 A | 11/1991 | Woog |
| 5,063,922 A | 11/1991 | Hakkinen |
| 5,067,655 A | 11/1991 | Farago |
| 5,076,266 A | 12/1991 | Babaev |
| 5,104,042 A | 4/1992 | McKown |
| 5,115,805 A | 5/1992 | Bommannan |
| 5,134,993 A | 8/1992 | van der L |
| 5,143,588 A | 9/1992 | Liboff |
| 5,152,289 A | 10/1992 | Viebach |
| 5,163,433 A | 11/1992 | Kagawa |
| 5,171,215 A | 12/1992 | Flanagan |
| 5,172,692 A | 12/1992 | Kulow et al. |
| 5,186,162 A | 2/1993 | Talish |
| 5,197,946 A | 3/1993 | Tachibana |
| 5,211,160 A | 5/1993 | Talish |
| 5,219,401 A | 6/1993 | Cathignol |
| 5,231,975 A | 8/1993 | Bommannan |
| 5,259,384 A | 11/1993 | Kaufman |
| 5,269,291 A | 12/1993 | Carter |
| 5,309,898 A | 5/1994 | Kaufman |
| 5,314,441 A | 5/1994 | Cusack |
| 5,315,998 A | 5/1994 | Tachibana |
| 5,316,000 A | 5/1994 | Chapelon |
| 5,318,014 A | 6/1994 | Carter |
| 5,323,769 A | 6/1994 | Bommannan |
| 5,324,255 A | 6/1994 | Passafaro |
| 5,345,940 A | 9/1994 | Seward |
| 5,347,998 A | 9/1994 | Hodson |
| 5,362,309 A | 11/1994 | Carter |
| 5,374,266 A | 12/1994 | Kataoka |
| 5,376,855 A | 12/1994 | Suganuma |
| 5,380,411 A | 1/1995 | Schlief |
| 5,386,940 A | 2/1995 | Berfield |
| 5,393,296 A | 2/1995 | Rattner |
| 5,431,663 A | 7/1995 | Carter |
| 5,437,606 A | 8/1995 | Tsukamoto |
| 5,456,258 A | 10/1995 | Kondo |
| 5,515,841 A | 5/1996 | Robertson |
| 5,515,842 A | 5/1996 | Ramseyer |
| 5,516,043 A | 5/1996 | Manna |
| 5,520,166 A | 5/1996 | Ritson |
| 5,520,612 A | 5/1996 | Winder |
| 5,523,058 A | 6/1996 | Umermura |
| 5,527,350 A | 6/1996 | Grove |
| 5,529,572 A | 6/1996 | Spector |
| 5,545,124 A | 8/1996 | Krause |
| 5,547,459 A | 8/1996 | Kaufman |
| 5,551,416 A | 9/1996 | Stimpson |
| 5,554,172 A | 9/1996 | Horner |
| 5,556,372 A | 9/1996 | Talish |
| 5,573,497 A | 11/1996 | Chapelon |
| 5,611,993 A | 3/1997 | Babaev |
| 5,616,140 A | 4/1997 | Prescott |
| 5,618,275 A | 4/1997 | Bock |
| 5,626,554 A | 5/1997 | Ryaby |
| 5,630,828 A | 5/1997 | Mawhirt |
| 5,643,179 A | 7/1997 | Fujimoto |
| 5,656,016 A | 8/1997 | Ogden |
| 5,658,323 A | 8/1997 | Miller |
| 5,664,570 A | 9/1997 | Bishop |
| 5,688,224 A | 11/1997 | Forkey |
| 5,699,805 A | 12/1997 | Seward |
| 5,702,360 A | 12/1997 | Dieras |
| 5,707,402 A | 1/1998 | Heim |
| 5,707,403 A | 1/1998 | Grove |
| 5,725,494 A | 3/1998 | Brisken |
| 5,730,705 A | 3/1998 | Talish |
| 5,735,811 A | 4/1998 | Brisken |
| 5,743,863 A | 4/1998 | Chapelon |
| 5,752,924 A | 5/1998 | Kaufman |
| 5,762,616 A | 6/1998 | Talish |
| 5,785,972 A | 7/1998 | Tyler |
| 5,807,285 A | 9/1998 | Vaitekunas |
| 5,835,678 A | 11/1998 | Li |
| 5,843,139 A | 12/1998 | Goedeke |
| 5,875,976 A | 3/1999 | Nelson |
| 5,879,314 A | 3/1999 | Peterson |
| 5,879,364 A | 3/1999 | Bromfield |
| 5,882,302 A | 3/1999 | Driscoll |
| 5,894,841 A | 4/1999 | Voges |
| 5,895,362 A | 4/1999 | Elstrom |
| 5,904,659 A | 5/1999 | Duarte |
| 5,947,921 A | 9/1999 | Johnson |
| 5,957,882 A | 9/1999 | Nita |
| 5,960,792 A | 10/1999 | Lloyd |
| 5,964,223 A | 10/1999 | Baran |
| 5,989,245 A | 11/1999 | Prescott |
| 6,001,069 A | 12/1999 | Tachibana |

(56) References Cited

U.S. PATENT DOCUMENTS

| | | |
|---|---|---|
| 6,007,499 A | 12/1999 | Martin |
| 6,014,970 A | 1/2000 | Irvi |
| 6,024,718 A | 2/2000 | Chen |
| 6,026,808 A | 2/2000 | Armer |
| 6,027,495 A | 2/2000 | Miller |
| 6,036,661 A | 3/2000 | Schwarze |
| 6,041,253 A | 3/2000 | Kost |
| 6,061,597 A | 5/2000 | Rieman |
| 6,076,519 A | 6/2000 | Johnson |
| 6,083,159 A | 7/2000 | Driscoll |
| 6,095,141 A | 8/2000 | Armer |
| 6,098,620 A | 8/2000 | Lloyd |
| 6,102,298 A | 8/2000 | Bush |
| 6,104,952 A | 8/2000 | Tu |
| 6,106,547 A | 8/2000 | Huei-Jung |
| 6,113,558 A | 9/2000 | Rosenschein |
| 6,113,570 A | 9/2000 | Siegel |
| RE36,939 E | 10/2000 | Tachibana |
| 6,139,320 A | 10/2000 | Hahn |
| 6,158,388 A | 12/2000 | Wenstrand |
| 6,158,431 A | 12/2000 | Poole |
| 6,161,536 A | 12/2000 | Redmon et al. |
| 6,176,839 B1 | 1/2001 | Deluis |
| 6,186,963 B1 | 2/2001 | Schwarze |
| 6,190,315 B1 | 2/2001 | Kost |
| 6,190,336 B1 | 2/2001 | Duarte |
| 6,206,842 B1 | 3/2001 | Tu |
| 6,206,843 B1 | 3/2001 | Lger |
| 6,231,528 B1 | 5/2001 | Kaufman |
| 6,234,990 B1 | 5/2001 | Rowe |
| 6,251,099 B1 | 6/2001 | Kollias |
| 6,254,294 B1 | 7/2001 | Muhar |
| 6,273,864 B1 | 8/2001 | Duarte |
| 6,296,630 B1 | 10/2001 | Altman et al. |
| 6,311,573 B1 | 11/2001 | Bhardwaj |
| 6,314,318 B1 | 11/2001 | Petty |
| 6,321,109 B2 | 11/2001 | Ben-Haim |
| 6,322,527 B1 | 11/2001 | Talish |
| 6,325,769 B1 | 12/2001 | Klopotek |
| 6,392,327 B1 | 5/2002 | Lewis |
| 6,450,417 B1 | 9/2002 | Gipson |
| 6,458,109 B1 | 10/2002 | Henley |
| 6,478,754 B1 | 11/2002 | Babaev |
| 6,500,133 B2 | 12/2002 | Martin et al. |
| 6,533,484 B1 | 3/2003 | Osei |
| 6,533,803 B2 | 3/2003 | Babaev |
| 6,559,365 B2 | 5/2003 | Wilfer |
| 6,569,099 B1 * | 5/2003 | Babaev ............... A61M 3/0275 600/437 |
| 6,583,071 B1 | 6/2003 | Weidman |
| 6,601,581 B1 | 8/2003 | Babaev |
| 6,623,444 B2 | 9/2003 | Babaev |
| 6,659,365 B2 | 12/2003 | Gipson |
| 6,663,554 B2 | 12/2003 | Babaev |
| 6,666,431 B2 | 12/2003 | McCusker |
| 6,723,064 B2 | 4/2004 | Babaev |
| 6,732,744 B2 | 5/2004 | Olshavsky |
| 6,761,729 B2 | 7/2004 | Babaev |
| 6,772,967 B1 | 8/2004 | Bontems |
| 6,830,556 B2 | 12/2004 | Harmon |
| 6,916,296 B2 | 7/2005 | Soring |
| 6,960,173 B2 | 11/2005 | Babaev |
| 6,964,647 B1 | 11/2005 | Babaev |
| 7,025,735 B2 | 4/2006 | Soring |
| 7,316,664 B2 | 1/2008 | Kadziauskas |
| 7,431,704 B2 | 10/2008 | Babaev |
| 7,572,268 B2 | 8/2009 | Babaev |
| 7,662,177 B2 | 2/2010 | Babaev |
| 7,713,218 B2 | 5/2010 | Babaev |
| 7,729,779 B2 | 6/2010 | Babaev |
| 7,753,285 B2 | 7/2010 | Babaev |
| 7,780,095 B2 | 8/2010 | Babaev |
| 7,785,277 B2 | 8/2010 | Babaev |
| 7,785,278 B2 | 8/2010 | Babaev |
| 7,830,070 B2 | 11/2010 | Babaev |
| 7,901,388 B2 | 3/2011 | Babaev |
| 7,914,470 B2 | 3/2011 | Babaev |
| 8,074,896 B2 | 12/2011 | Ricciardi |
| 8,491,521 B2 | 7/2013 | Peterson |
| 8,647,720 B2 | 2/2014 | Staunton |
| D733,319 S | 6/2015 | Somers et al. |
| D733,321 S | 6/2015 | Somers et al. |
| 9,365,341 B2 | 6/2016 | Bruna |
| 2002/0000763 A1 | 1/2002 | Jones |
| 2002/0049462 A1 * | 4/2002 | Friedman ........ A61B 17/320068 606/169 |
| 2002/0049463 A1 | 4/2002 | Friedman |
| 2002/0062093 A1 | 5/2002 | Soring |
| 2002/0080206 A1 | 6/2002 | Lin |
| 2002/0138036 A1 | 9/2002 | Babaev |
| 2002/0150539 A1 | 10/2002 | Unger |
| 2002/0156400 A1 | 10/2002 | Babaev |
| 2002/0177846 A1 | 11/2002 | Mulier et al. |
| 2003/0023193 A1 | 1/2003 | Soring |
| 2003/0125660 A1 | 7/2003 | Moutafis |
| 2003/0144627 A1 | 7/2003 | Woehr |
| 2003/0153961 A1 | 8/2003 | Babaev |
| 2003/0171701 A1 | 9/2003 | Babaev |
| 2003/0195644 A1 | 10/2003 | Borders |
| 2003/0216687 A1 | 11/2003 | Hwang |
| 2003/0236560 A1 | 12/2003 | Babaev |
| 2004/0015105 A1 | 1/2004 | Ito |
| 2004/0028552 A1 | 2/2004 | Bhardwaj |
| 2004/0030254 A1 | 2/2004 | Babaev |
| 2004/0034982 A1 | 2/2004 | Wieber |
| 2004/0055376 A1 | 3/2004 | Thompson |
| 2004/0068297 A1 | 4/2004 | Palti |
| 2004/0073175 A1 | 4/2004 | Jacobsen |
| 2004/0076175 A1 | 4/2004 | Patenaude |
| 2004/0091541 A1 | 5/2004 | Unger |
| 2004/0162509 A1 | 8/2004 | Sakurai |
| 2004/0186384 A1 | 9/2004 | Babaev |
| 2004/0211260 A1 * | 10/2004 | Girmonsky .......... A61B 5/0215 73/579 |
| 2005/0075587 A1 | 4/2005 | Vago |
| 2005/0075620 A1 | 4/2005 | Iger |
| 2005/0086023 A1 * | 4/2005 | Ziegler ................. G01N 29/07 702/127 |
| 2005/0203444 A1 | 9/2005 | Schonenberger |
| 2006/0025716 A1 | 2/2006 | Babaev |
| 2006/0058710 A1 | 3/2006 | Babaev |
| 2007/0016110 A1 | 1/2007 | Babaev et al. |
| 2007/0088245 A1 | 4/2007 | Babaev et al. |
| 2007/0090205 A1 | 4/2007 | Kunze |
| 2007/0299369 A1 | 12/2007 | Babaev |
| 2008/0051693 A1 | 2/2008 | Babaev |
| 2008/0110263 A1 * | 5/2008 | Klessel ............... G01S 7/52085 73/602 |
| 2008/0132888 A1 | 6/2008 | Iida |
| 2008/0177221 A1 | 7/2008 | Millerd |
| 2008/0183109 A1 | 7/2008 | Babaev |
| 2008/0183200 A1 | 7/2008 | Babaev |
| 2008/0214965 A1 | 9/2008 | Peterson et al. |
| 2008/0234708 A1 * | 9/2008 | Houser .......... A61B 17/320092 606/169 |
| 2008/0243047 A1 | 10/2008 | Babaev |
| 2008/0243048 A1 | 10/2008 | Babaev |
| 2008/0306501 A1 | 12/2008 | Babaev |
| 2009/0018491 A1 | 1/2009 | Babaev |
| 2009/0018492 A1 | 1/2009 | Babaev |
| 2009/0024076 A1 | 1/2009 | Babaev |
| 2009/0043248 A1 | 2/2009 | Peterson |
| 2009/0177122 A1 | 7/2009 | Peterson |
| 2009/0177123 A1 | 7/2009 | Peterson |
| 2009/0187136 A1 | 7/2009 | Babaev |
| 2009/0200394 A1 | 8/2009 | Babaev |
| 2009/0200396 A1 | 8/2009 | Babaev |
| 2009/0222037 A1 | 9/2009 | Babaev |
| 2009/0254005 A1 | 10/2009 | Babaev |
| 2010/0022919 A1 | 1/2010 | Peterson |
| 2010/0076349 A1 | 3/2010 | Babaev |
| 2010/0249882 A1 | 9/2010 | Houben |
| 2012/0010506 A1 | 1/2012 | Ullrich |
| 2012/0223160 A1 | 9/2012 | Goodwin |

(56) References Cited

U.S. PATENT DOCUMENTS

| | | |
|---|---|---|
| 2013/0053697 A1 | 2/2013 | Holl |
| 2014/0276069 A1 | 9/2014 | Amble |
| 2015/0148712 A1 | 5/2015 | Loven |

FOREIGN PATENT DOCUMENTS

| | | |
|---|---|---|
| CA | 2436812 | 8/2002 |
| CN | 1466445 | 1/2004 |
| EP | 0 202 844 | 11/1985 |
| EP | 0416106 | 3/1991 |
| EP | 0 437 155 | 7/1991 |
| EP | 0 657 226 | 11/1994 |
| EP | 0 619 104 | 3/2002 |
| EP | 1 199 047 | 4/2002 |
| EP | 0 1564009 | 8/2005 |
| GB | 2099710 A | 12/1982 |
| GB | 2101500 A | 1/1983 |
| JP | 3-73168 | 3/1991 |
| JP | 417844 A | 4/1992 |
| JP | 9135908 | 5/1997 |
| JP | 2000237275 A2 | 9/2000 |
| SU | 878268 | 11/1981 |
| SU | 910157 | 3/1982 |
| SU | 1106485 | 10/1982 |
| SU | 1176968 | 9/1985 |
| SU | 1237261 A2 | 6/1986 |
| SU | 1827239 | 5/1990 |
| SU | 1704847 A2 | 1/1992 |
| WO | WO94-06380 | 3/1994 |
| WO | WO 96-35383 | 11/1996 |
| WO | WO02-24150 | 3/2002 |
| WO | WO 02-028350 A2 | 4/2002 |
| WO | WO02-060525 | 8/2002 |
| WO | WO02-095675 | 11/2002 |
| WO | WO 2007-002598 | 1/2007 |
| WO | WO 2009/005980 | 1/2009 |
| WO | WO 2009/102976 | 8/2009 |
| WO | WO 2016/033041 | 3/2016 |

OTHER PUBLICATIONS

Written Opinion for International Application No. PCT/US06/24833, dated Feb. 22, 2007, 5 pages.
Zharov et al, "Comparison Possibilities of Ultrasound and Its Combination with Laser in Surgery and Therapy", pp. 331-339, In Biomedical Optoacoustics.
Asakawa, M. et al., "WBN-Kob-Ht Rats Spontaneously Develop Dermatitis Under Conventional Conditions: Another Possible Model for Atopic Dermatitis," Exp. Anim.,54(5): pp. 461-465 (2005).
Bisno, Alan.L., et al., "Murine Model of Recurrent Group G Streptococcal Cellulitis: No Evidence of Proective Immunity," Infection and Immunity, vol. 65 No. 12, pp. 4926-4930 © 1997.
Brooks, R.R., , "Canine Carrageenin-Induced Actue Paw Inflammation Model and its Response to Nonsteroidal Antiinflammatory Drugs," J. Parrnacol Methods, 25, pp. 275-283 © 1991.
Chen, L. et al., The Disease Progression in the Keratin 14 IL-4-transgenic Mouse Model of Atopic Dermatitis Parallels the Up-regulation ofB Cell Activation Molecules, Proliferation and Surface and Serum lg;E, Clin, Exp. Immunolo, 142: 21-30 © 2005.
Chinese Office Action, dated May 22, 2009 for Chinese Application No. 2006800227860, 9 pages.
Department of Health & Human Services Letter dated Jun. 25, 2004, 3 pages.
Department of Health & Human Services Letter Dated May 17, 2005, 3 pages.
Zharov et al., Design and Application of Low-Frequency Ultrasound and Its Combination With Laser Radiation in Surgery and Therapy, Critical Reviews in Biomedical Engineering; No. 4, 2000, pp. 502-519.
Dong, Cheng, et al., "MAP Kinases in the Immune Response," Annu. Rev. Immunol., 20: 55-72 © 2002.
Ennis, William J. et al. "Ultrasound Therapy for Recalcitrant Diabetic Foot Ulcers: Results of a Randomized, Double-Blind, Controlled, Multicenter Study", Ostomy/Wound Management 2005; 51(8): pp. 24-39.
European Examination Report for European Application No. 01 973 554.8, dated Feb. 9, 2010, 3 pages.
European Examination Report for European Application No. 08 866 666.4, dated Mar. 22, 2011, 5 pages.
European Office Action from European Application No. EP01973544.8 dated Dec. 16, 2011, 4 pages.
European Search Report corresponding to European Application No. 01973544.8-2107—U.S. Pat. No. 130, 096, Applicant Advanced Medical Applications Inc., dated Sep. 13, 2004, 5 pages.
European Search Report, European Application No. 01973 544.8-2107—U.S. Pat. No. 130,096, dated Sep. 13, 2004, 5 pages.
European Search Report for European App. 0270923 5, dated Apr. 4, 2006.
European Supplementary Search Report corresponding to European Application No. 01973544, dated Sep. 1, 2004.
Examination Report, dated Dec. 5, 2007, for Indian App. 1078-MUMNP-2005.
Examination Report, dated Jul. 1, 2008, for European App. 02709235.2-2305, 4 pages.
Examination Report, dated Nov. 21, 2007, for European App. 02709235.2-2305, 4 pages.
Hammer, Robert E. et al. , "Spontaneous Inflammatory Disease in Transgenic Rats Expressing HLA-B27 and Human $\beta_2$m: An Animal Model ofHLA-B27-Associated Human Disorders," Cell, vol. 63, pp. 1099-1112, © 1990.
Haqqi, Tariq M., et al., "Restricted Heterogeneity in T-cell Antigen Receptor $V_\beta$ Gene Usage in the Lymph Nodes and Arthritic Joints of Mice," Proc. Natl. Acad. Sci. USA, vol. 89: 1253-1255, Feb. 1992.
Hurvitz, A.l., "Animal Model of Human Disease, Pemphigus Vulgaris, Animal Model: Canine Pemphigus Vulgaris," American Journal of Pathology, 98(3): 861-864 (1980).
International Search Report for EP 04749758.1-2319, dated Mar. 30, 2011, 5 pages.
International Search Report for PCT/US2004/010448, dated Nov. 10, 2004, 4 pages.
International Search Report for PCT/US01/31226, dated Sep. 11, 2002, 1 page.
International Search Report for PCT/US01/30096, dated Sep. 25, 2002, 1 page.
International Search Report for PCT/US02/02724, dated Dec. 11, 2002, 3 pages.
International Search Report for PCT/US06/24833, dated Feb. 22, 2007, 1 page.
International Search Report for PCT/US2007/026251, dated May 7, 2008, 2 pages.
International Search Report for PCT/US2008/000151, dated Apr. 21, 2008, 4 pages.
International Search Report for PCT/US95/14926, dated Feb. 27, 1996, 1 page.
Iraniha, Seed, et al. "Determination of Burn Depth With Noncontact Ultrasonography," J. Burn Care Rehabil., 21:333-338, Jul./Aug. 2000.
Janeway, Charles A. et al., "Innate Immune Recognition", Annual Review of Immunology 20: 197-216, © 2002.
Japanese Notification of Reasons for Rejection from Japanese Application No. 2008-518449 dated Jul. 29, 2011.
Japanese Office Action, dated Dec. 18, 2009 for Japanese Application No. 2002-528187.
Japanese Office Action, dated Jul. 29, 2010 for Japanese Application No. 2002-528187.
Bina, Joe et al. "Animal Models of Rheumatoid Arthritis," Molecular Medicine Today, vol. 5, Aug. 1999, pp. 367-369.
Keffer, Jeanne , "Transgenic Mice Expressing Human Tumour Necrosis Factor: A Predictive Genetic Model of Arthritis," The EMBO Journal, vol. 10, No. 13, pp. 4025-4031 (1991).
Liu, Z. et al., "Immunopathological Mechanisms of Acantholysis in Pemphigus Vulgaris: An Explanation by Ultrastructural Observations," The Journal of Investigative Dermatology, © 2004.

(56) References Cited

OTHER PUBLICATIONS

Nishimuta, K. et al., "Effects of Metronidazole and Tinidazole Ointments on Models for Inflammatory Dermatitis in Mice," Arch. Dermatol. Res., 294: 544-551 (2003).
Office Action and Machine Translation Summary of Office Action, dated Apr. 25, 2006, for Mexican App. PA-a-2003-002535, 3 pages.
Office Action and Machine Translation Summary of Office Action, dated Jul. 7, 2008, for Mexican App. PA-a-2003-002535, 3 pages.
Office Action dated Apr. 24, 2007, for Japanese App. No. 2002-560715 now JP-4,164,582, 3 pages.
Office Action, dated Apr. 20, 2007, for Chinese App. 01816263.0, 8 pages.
Office Action, dated Aug. 14, 2007, for Canadian App. 2,421,798, 3 pages.
Office Action, dated Aug. 5, 2009, for Canadian App. 2,421,798, 3 pages.
Office Action, dated Jan. 14, 2010, for Canadian App. 2,436,812, 3 pages.
Office Action, dated Jan. 18, 2008, for Chinese App. 01816263.0, 11 pages.
Office Action, dated May 18, 2006, for Canadian App. 2,421,798, 4 pages.
Office Action, dated May 3, 2006, for Canadian App. 2,43 6,812, 2 pages.
Office Action, dated Nov. 2, 2009, for Canadian App. 2,521,117, 3 pages.
Office Action, dated Nov. 5, 2009, for Japanese App. 2006-509708, 3 pages.
Office Action, dated Sep. 12, 2006, for Canadian App. 2,463,600, 3 pages.
Office Action, dated Sep. 26, 2007, for Canadian App. 2,521,117, 3 pages.
Pelletier, Jean-Pierre et al., "In vivo Suppression of Early Experimental Osteoarthritis by Interleukin-1 Receptor Antagonist Using Gene Therapy," Arthritis & Rheumatism, vol. 40, No. 6, pp. 1012-1019, Jun. 1997.
Schon, Michael P. "Animal Models of Psoriasis—What Can We Learn from Them?", The Journal of Investigative Dermatology, 112(4): 405-410 © 1999.
Trentham, David E., Autoimmunity to Type II Collagen: An Experimental Model of Arthritis, The Journal of Experimental Medicine, vol. 146, 1977.
Wooley, Paul H. , "Type II Collagen-Induced Arthritis in Mice, I. Major Histocompatibility Complex (I Region) Linkage and Antibody Correlates," J. Exp. Med., vol. 154, pp. 688-700, Sep. 1981. XP-002294548, Abstract corresponding to SU 914099.
Yamamoto, Toshiyuki, "Characteristics of Animal Models for Scleroderma," Current Rheumatology Reviews, vol. 1, No. 1, pp. 101-109, (2005).
Application and File History for U.S. Appl. No. 09/704,099, filed Nov. 1, 2000, now U.S. Pat. No. 6,601,581, issued Aug. 5, 2003, Inventor: Eilaz Babaev.
Application and File History for U.S. Appl. No. 09/774,145, filed Jan. 30, 2001, now U.S. Pat. No. 6,960,173, issued Nov. 1, 2005, Inventor: Eilaz Babaev.
Application and File History for U.S. Appl. No. 09/840,416, filed Apr. 23, 2001, now U.S. Pat. No. 6,478,754, issued Nov. 12, 2002, Inventor: Eilaz Babaev.
Application and File History for U.S. Appl. No. 10/214,339, filed Aug. 7, 2002, now U.S. Pat. No. 6,663,554, issued Dec. 16, 2003, Inventor: Eilaz Babaev.
Application and File History for U.S. Appl. No. 09/669,312, filed Aug. 7, 2002, now U.S. Pat. No. 6,569,099, issued May 27, 2003, Inventor: Eilaz Babaev.
Application and File History for U.S. Appl. No. 10/409,272, filed Apr. 7, 2003, now U.S. Pat. No. 8,235,919, issued Aug. 7, 2012, Inventor: Eilaz Babaev.
Application and File History for U.S. Appl. No. 10/815,384, filed Apr. 1, 2004, now U.S. Pat. No. 7,914,470, issued Mar. 29, 2011, Inventor: Eilaz Babaev.
International Search Report, International Application No. PCT/US2014/066159, dated Mar. 24, 2015, 14 pages.
Examination Report for EP 04749758.1-2319, dated Apr. 30, 2010, 3 pages.
Clark, Richard A.F., The Molecular and Cellular Biology of Wound Repair, Second Edition, *Wound Repair: Overview and General Considerations*, Chapter 1, pp. 3-49.
International Preliminary Report on Patentability, International Application No. PCT/US2014/066159, dated Jun. 9, 2016, 10 pages.
European Search Report, Application No. 14865354.6, dated Jun. 28, 2017, 8 pages.
International Search Report and Written Opinion, International Application No. PCT/US17/44323, dated Oct. 25, 2017, 16 pages.
Amemark, Quick Reference Guide, Jun. 2015, 1 page.
Australian Examination Report, Application No. 2014355072, dated Aug. 29, 2018, 5 pages.
International Preliminary Report on Patentability, Application No. PCT/US2017/044323, dated Feb. 7, 2019, 10 pages.
European Examination Report, Patent Application No. 14865354.6, dated Jun. 18, 2019, 7 pages.
Australian Examination Report, Patent Application No. 2019219713, dated Mar. 19, 2020, 5 pages.

* cited by examiner

SYSTEMS AND METHODS FOR PRODUCING AND DELIVERING ULTRASONIC THERAPIES FOR WOUND TREATMENT AND HEALING

RELATED APPLICATION

This application is a continuation of application Ser. No. 14/546,808 filed Nov. 18, 2014, which claims the benefit of U.S. Provisional Patent App. No. 61/909,086 filed Nov. 26, 2013, which is incorporated herein by reference in its entirety.

TECHNICAL FIELD

Embodiments relate generally to ultrasound therapy systems and methods and more particularly to a non-contact, low-frequency, highly efficient ultrasound therapy system that delivers ultrasonic therapy treatments via a mist to a patient wound to promote wound healing.

BACKGROUND

Use of ultrasonic waves to promote healing of wounds has become more common in recent years as its benefits are better understood and this type of therapy becomes more widely utilized. In general, ultrasonic waves have been used in medical applications for a long time, including diagnostics, therapy, and industrial applications.

A number of innovative ultrasound therapy systems and devices have previously been developed including non-contact, ultrasound mist therapy devices by the assignee of the current application, Celleration, Inc. These systems and devices have been widely used for medical treatments in medical facilities around the world. See, for example, co-owned U.S. Pat. No. 6,569,099, entitled ULTRASONIC METHOD AND DEVICE FOR WOUND TREATMENT, which is incorporated herein by reference in its entirety. Unlike most conventional wound therapies that are limited to treatment of the wound surface, Celleration, Inc., developed therapies in which ultrasound energy and atomized normal saline solutions were used to stimulate the cells within and below the wound bed to aid in the healing process.

Although these ultrasound therapies have been effective, devices, systems and methods providing improved ultrasonic therapies that are more accessible, safer to administer to patients, and more efficient in delivery of ultrasound energy have been widely desired.

SUMMARY

Embodiments relate to non-contact, low-frequency, highly efficient ultrasound therapy devices, systems and methods that deliver ultrasonic therapy treatments via a mist to a patient wound to promote wound healing. One embodiment is directed to a non-contact, medical ultrasound therapy system for generating and controlling low frequency ultrasound. The ultrasound therapy system includes a treatment wand including an ultrasonic transducer, a generator unit, and a cable coupling the treatment wand to the generator unit. The generator unit generates electric power output to drive the ultrasonic transducer and includes a digital frequency generator, wherein the generator unit digitally controls energy output at resonance frequency of the ultrasonic transducer.

Another embodiment is directed to a highly efficient ultrasonic generator unit. The ultrasonic generator unit includes an ultrasonic driver with digital controls to maintain system displacement at resonance frequency of a transducer coupled to the ultrasonic generator unit. The ultrasonic driver in this embodiment includes a microprocessor, a digital frequency generator, and a phase detector.

A further embodiment is directed to an ultrasonic system. The ultrasonic system includes a user interface controlled by a first microprocessor, a treatment device including an ultrasonic transducer, and a generator unit including an ultrasonic driver controlled by a second microprocessor. In this embodiment both the first microprocessor and the second microprocessor are configured to individually suspend operation of the ultrasonic system in fault condition situations.

A further embodiment is directed to a method for digitally generating and controlling low frequency ultrasound used in a non-contact medical ultrasound therapy system. The method includes performing a power on self-test to an ultrasonic therapy system that includes a treatment wand containing an ultrasonic transducer and a generator unit containing an ultrasonic driver. The method further includes performing a frequency sweep using a sine wave to determine a resonance frequency of the ultrasonic transducer by evaluating and looking for a relative minimum impedance of the ultrasonic transducer. The method further includes adjusting the digital frequency generator output frequency based on voltage vs. current phase angle so that a frequency lockup is maintained at the resonance frequency, and monitoring voltage and phase detection circuits of the ultrasonic therapy system for phase difference.

BRIEF DESCRIPTION OF THE DRAWINGS

The invention may be more completely understood in consideration of the following detailed description of various embodiments of the invention in connection with the accompanying drawings, in which.

DETAILED DESCRIPTION OF THE DRAWINGS

Various embodiments may be embodied in other specific forms without departing from the essential attributes thereof, therefore, the illustrated embodiments should be considered in all respects as illustrative and not restrictive.

A need for a more accessible and safer ultrasonic therapy device and system for patients to use has been recognized in this disclosure. Further, many of the substantial technical obstacles to providing such a device based on the requirements of conventional ultrasound therapy devices are recognized and overcome by this disclosure. Specifically, making devices more readily accessible to additional patient populations has been a significant problem due to the very high voltage necessary to operate conventional devices. For example, some conventional ultrasound therapy devices have operated at about 700 Volts (V) peak-to-peak and 7 Watts (W) of energy. This has necessitated qualified oversight of therapy provision, as allowing patients to operate such a high voltage machine on their own might otherwise present a significant safety risk. Further, the energy requirements of conventional devices have made the possibility of a portable battery powered device, which could be used in a homecare environment, unfeasible. Ultrasound therapy systems described herein, however, overcome many or all of the technological obstacles of the past and provide a lower-power, safer, more efficient, and more accessible ultrasound therapy system. In embodiments, an ultrasound therapy system can be monitored and controlled to operate at or near resonant frequency (Fr), which can be more efficient that operating at or near anti-resonant frequency because it requires less voltage and is more efficient. Even battery powered systems are possible in certain embodiments. Accordingly, designs for new medical ultrasound devices, systems and methods incorporating various features, concepts and improvements, are described in the following detailed description.

Figure 1:
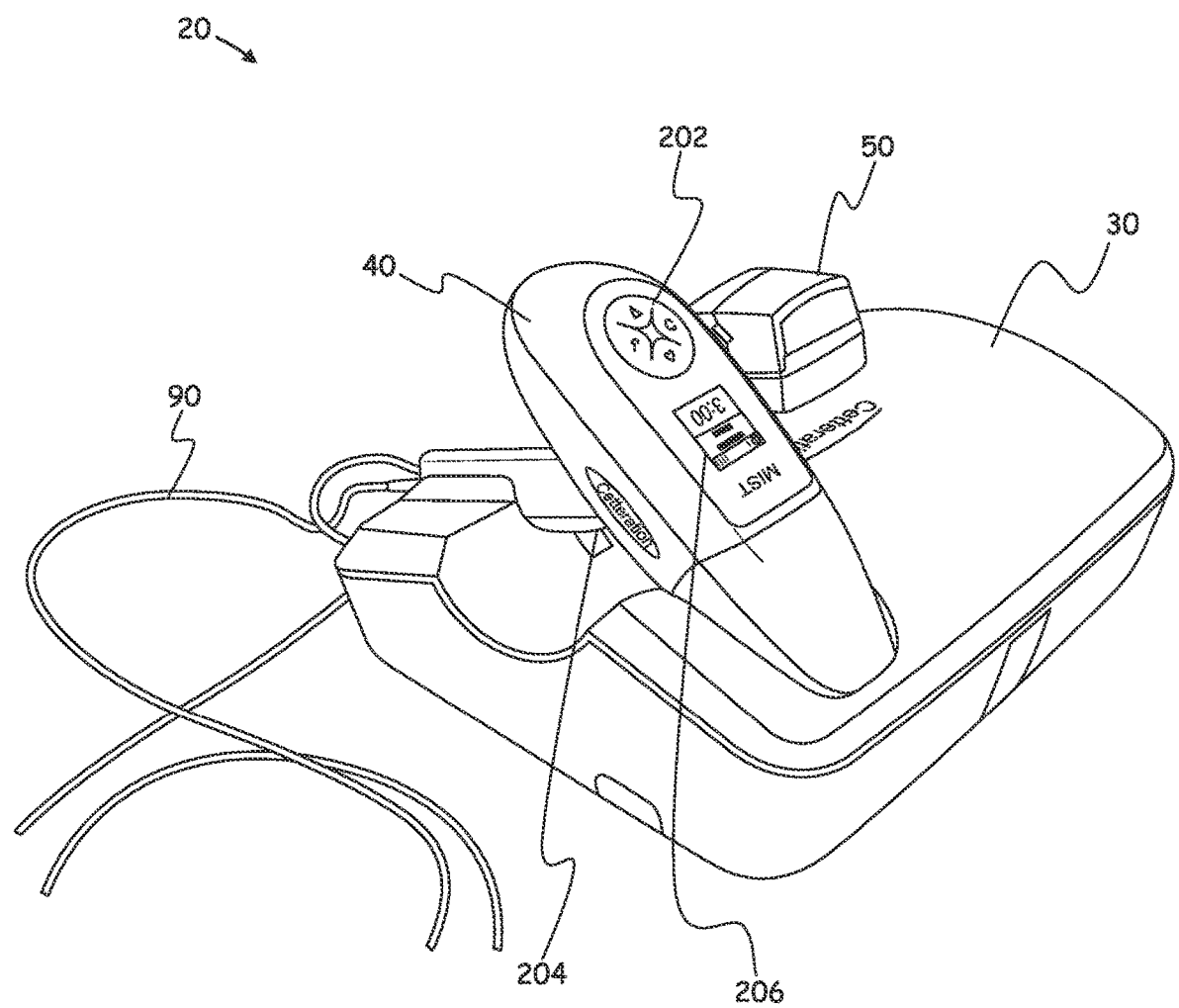
FIG. 1 is an ultrasound device of a system providing non-contact therapy to patient wounds via a low frequency ultrasound mist, according to an embodiment.
Figure 2:
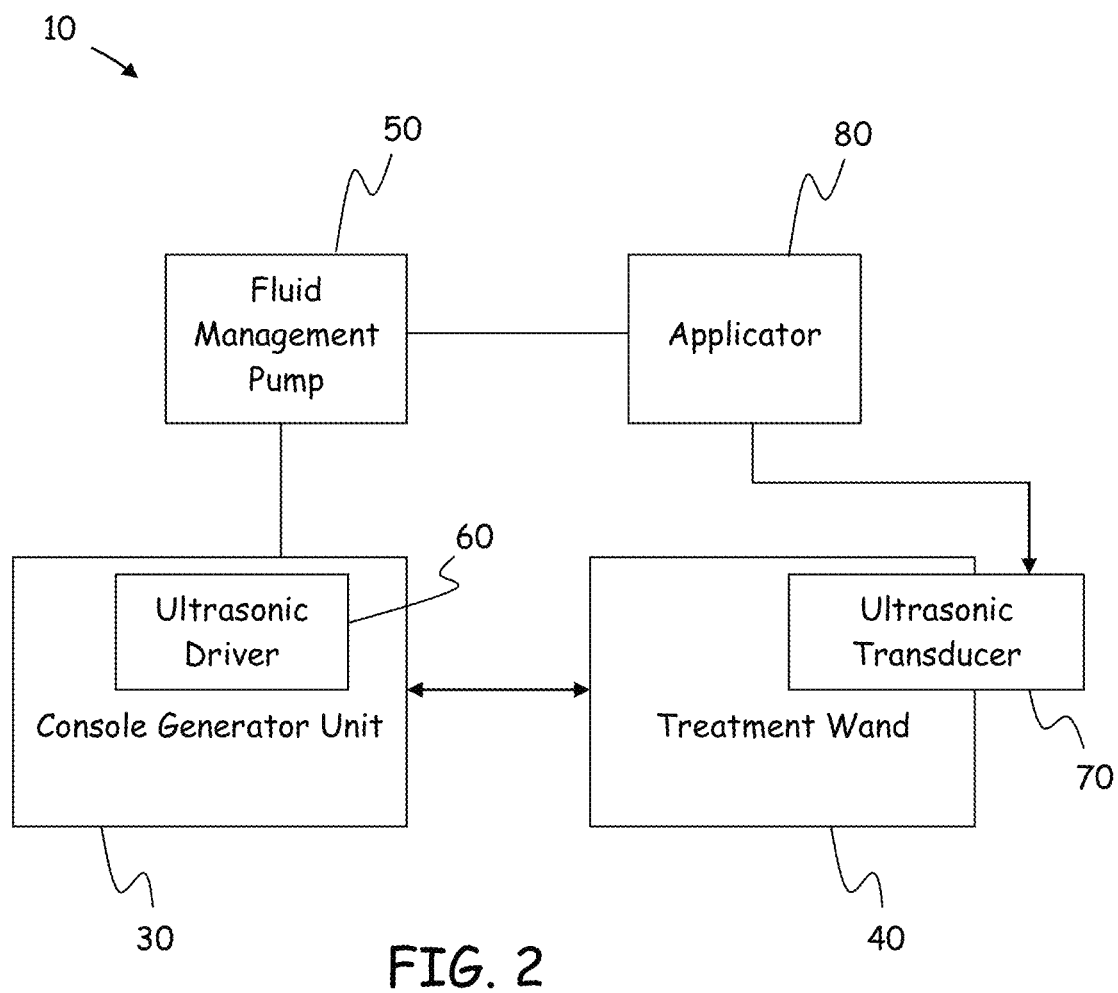
FIG. 2 is a diagram of an ultrasound therapy system, according to an embodiment.
Figure 3:
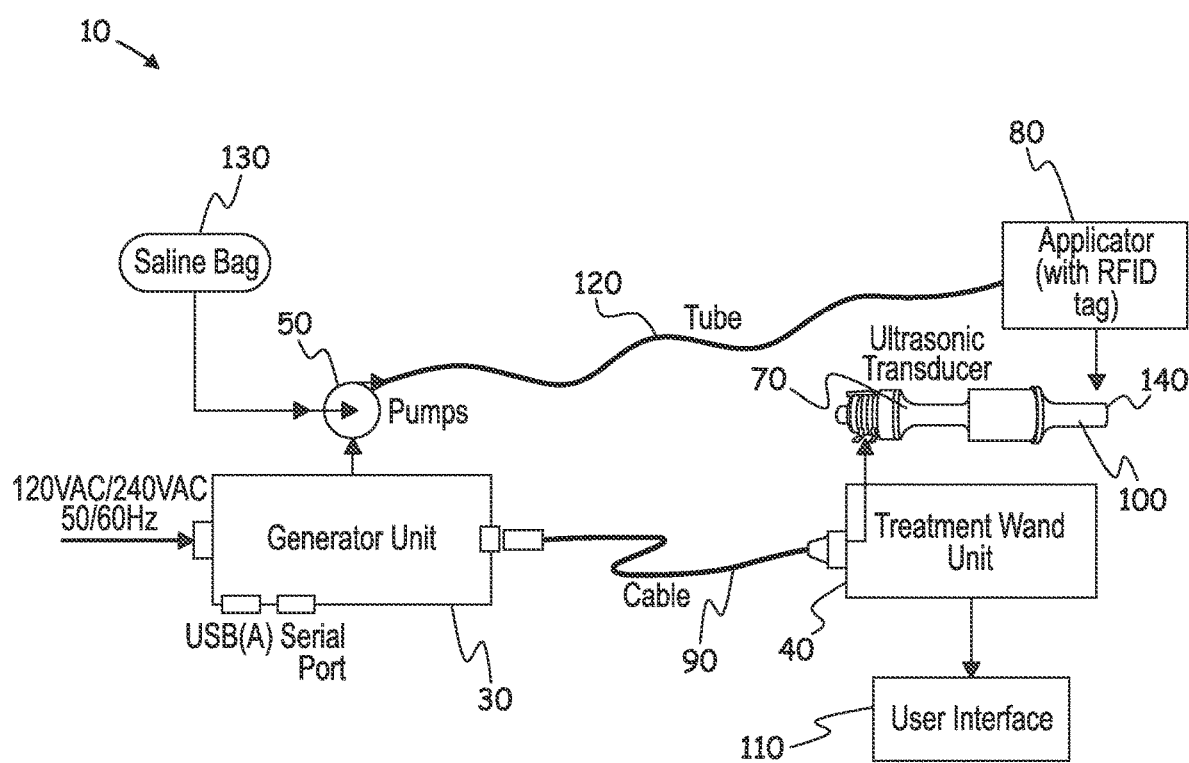
FIG. 3 is a diagram of an ultrasound therapy system, according to an embodiment.
Figure 4:
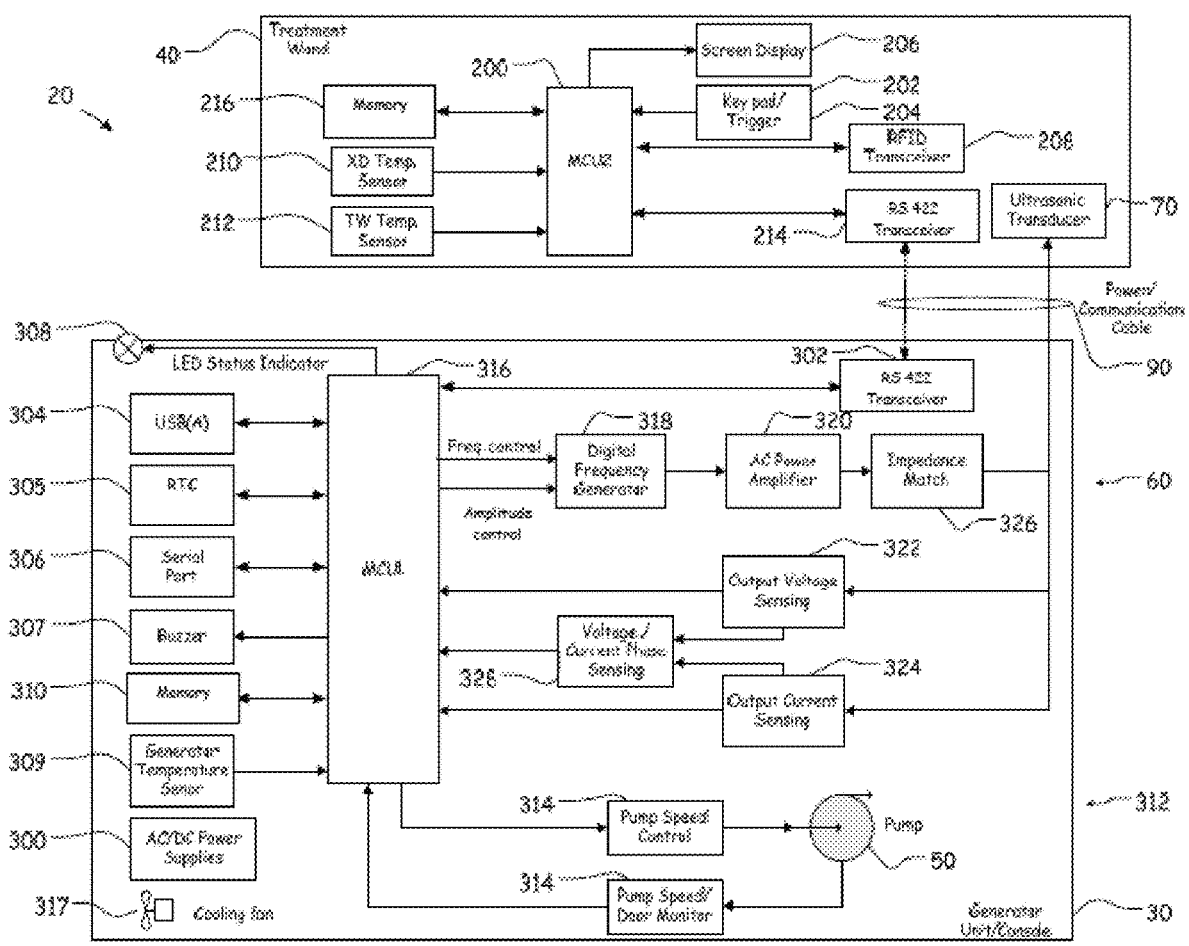
FIG. 4 is a diagram of an ultrasound device of a system providing for non-contact therapy to patient wounds via a low frequency ultrasound mist, according to an embodiment.

FIG. 1 shows an example of a medical ultrasound device 20 of an ultrasound therapy system 10 (refer, e.g., to FIG. 2) for delivering non-contact ultrasound therapies to patient wounds via a low-frequency ultrasound mist. Medical ultrasound device 20 comprises both a console/generator unit 30 for generating power and a treatment wand 40 for administering therapies. In general, generator unit 30 supplies power to an ultrasonic transducer within the treatment wand 40. Treatment wand 40 is ergonomically designed and can be generally pistol-shaped such that it may be conveniently positioned by a user to direct ultrasonic energy to a treatment area via atomized saline mist emitted from the end of treatment wand 40. Treatment wand 40 also can be balanced, such as in its physical design and weight distribution, to further improve and enhance ergonomics and usability. Generator unit 30 further comprises an external pump 50 which pumps saline or other fluid through a tube (not shown) attached to the end of treatment wand 40. Pump 50 depicted in FIG. 1 is a peristaltic pump but can comprise another suitable pump type or mechanism in other embodiments.

FIGS. 2 and 3 show high-level block diagrams of components of ultrasound therapy system 10. In general, as depicted in FIG. 2, system 10 comprises generator unit 30; treatment wand 40; fluid management pump 50; an ultrasonic driver 60; an ultrasonic transducer 70; and an applicator 80.

Generator unit 30 and treatment wand 40 are connected by a cable 90. Ultrasonic driver 60 comprises hardware mounted inside generator unit 30. A basic function of the ultrasonic driver 60 is to generate electric power output to drive ultrasonic transducer 70. Ultrasonic transducer 70 includes an acoustic horn 100 and related assembly mounted inside treatment wand 40. Ultrasonic transducer 70 converts and transfers input electrical power into vibrational mechanical (ultrasonic) energy that will be delivered to the treatment area (i.e. to a patient wound area via atomized saline). Treatment wand 40 contains the system's user interface 110 and controls for parameters of the treatment, though in other embodiments an additional or alternative user interface can be incorporated in generator unit 30. Treatment wand 40 is configured to appropriately position and hold applicator 80 relative to acoustic horn 100 for proper delivery of fluid during operation. The configuration also provides appropriate atomization of saline fluid and delivery of the resulting mist and ultrasound energy to a wound treatment area.

Fluid management pump 50 provides a fixed flow rate of saline or other fluid (e.g., about 0.9% normal saline in one embodiment) via a tube 120 to the distal tip 140 of ultrasonic transducer 70 from a saline bag 130 or other source, as appropriate. The saline fluid is delivered to the radial surface of transducer horn near its tip 140. The saline fluid is dispensed through an orifice on a superior surface of the horn 100, and a portion of the saline is displaced forward to the face of horn 100 and atomized by horn 100 when it is energized and operating. The remaining volume of fluid is fed to an inferior surface of ultrasonic transducer 70 via gravity and capillary action. When a sufficient volume of saline is accumulated, transducer tip 140 atomizes the saline into a plume. The atomized saline spray plume emanates from two points on the ultrasonic transducer 70, i.e., generally at the 12 o'clock and 6 o'clock positions given normal positioning of treatment wand 40 in operation, forming intersecting spray paths at approximately 5 mm from the front face of ultrasonic transducer 70 in some embodiments. In other embodiments, treatment wand 40, transducer 70, horn 100, tip 140 and/or other components can be designed to provide a differently sized or configured spray plume and paths.

FIG. 4 is a block diagram of a more detailed schematic of generator unit 30 and treatment wand 40 of ultrasound device 20. As can be understood from the following description, parameter control of voltage, current, duty cycle and phase angle is enabled, in some embodiments.

Treatment wand 40 houses ultrasonic transducer 70 and includes a microprocessor 200, various interface and sensing components, and an OLED display 206. Treatment wand 40 is pistol-shaped in embodiments to provide an improved ergonomic operator design, though other configurations can be implemented as may be advantageous in some applications. Treatment wand 40 comprises an acoustic horn assembly (e.g., piezo elements, back mass, horn and booster), ultrasonic transducer 70, microprocessor (MCU2) 200, user control key pad 202 and trigger 204, and an LCD screen display 206 that displays operational information and enables control and programming of the treatment therapy (see, e.g., FIG. 1). Treatment wand 40 also includes an RFID transceiver 208 in some embodiments, and RFID transceiver 208 can be used to identify applicator 80. This feature can be used to ensure that there is only a single use of a particular applicator 80 and to thereby deter unwanted reuse across multiple patients and/or treatments. Treatment wand 40 connects to generator unit 30 through cable 90. Cable 90 includes ultrasonic driver output power, communication components (such as those compatible with RS485, RS422 and/or other protocols) and power components (such as +5V and ground) in an embodiment, though other power and/or communications features can be implemented or facilitated by cable 90 in other embodiments. In one embodiment, 3.3V and 12.9V power can be generated from the 4.5V power provided by generator unit 30 for the electronics in the treatment wand 40. These example power characteristics can vary and are merely examples of one embodiment.

User interface 110 on treatment wand 40 includes key pad 202, trigger 204, and screen display 206. In some embodiments, display 206 can be a full-color OLED display, and key pad 202 can be a four button display, as shown in FIG. 1. The operator can configure and control device and system operation via key pad 202 and initiate the delivery of therapies by depressing a trigger switch 204.

Microprocessor 200 that controls user input requirements can also measure the internal temperature of treatment wand 40, or of transducer 70 or horn 100 more specifically, from ultrasonic transducer sensor 210 and treatment wand sensor 212. Microprocessor 200 also sends read/write information to applicator 80. Microprocessor 200 communicates with generator unit 30 via a communications protocol transceiver 214 (such as one compatible with RS485, RS422 and/or other protocols) and writes information to memory 216, which can be EEPROM, serial flash, or some other suitable memory. This information is stored and can be retrieved for understanding the use and performance of the system. Accordingly, greater detail can be given on data stored, how much, how long and how retrieved (USB upload/download by the user, service or other).

RFID transceiver 208 of treatment wand 40 can be used to communicate with an RFID tag (not shown) for applicator detection, as previously mentioned. The RFID tag can be located on applicator 80, and microprocessor 200 in treatment wand 40 can serve as an RFID reader and writer of the signals received via RFID transceiver 208. Specifically, an RFID controller can be used in treatment wand 40 for a Read/Write RF tag on applicator 80. In each new treatment, system 10 will require a new applicator 80. The RFID controller can read the ID tag of applicator 80 to identify if that particular applicator 80 is new or used. After a particular applicator 80 is used for a specified period of time, the RFID controller can write the information to an ID tag to identify that applicator 80 has been used to avoid reuse.

Microprocessor 200 of treatment wand 40, or another component of system 10, can be used to control input and output functions and perform control loops and calculations. Features of microprocessor 200 or another microprocessor or component of system 10 in some embodiments can include: an 80 MHz maximum frequency; 1.56 DMIPS/MHz (Dhrystone 2.1) performance; an operating voltage range of 2.3V to 3.6V; a 512K flash memory (plus an additional 12 KB of Boot Flash); a 128K SRAM memory; a USB 2.0-compliant full-speed device and On-The-Go (OTG) controller; up to 16-channel, 10-bit Analog-to-Digital Converter; six UART modules with RS-232, RS-485 and LIN support; and up to four SPI modules. These features are merely examples of one embodiment and can vary in other embodiments.

Ultrasonic transducer 70 generally comprises a piezoelectric ceramic element and metal horn 100 mounted in a sealed housing. The ultrasonic transducer input can be an AC voltage or AC current, or an AC voltage that results in a current, and the waveform can be a square form or sine form. The ultrasonic transducer output is mechanical vibration of the tip of transducer 70. The amount of energy output depends on tip 70 displacement, frequency, size and driver load (e.g., air or liquid mist). The ratio of output to input energy is referred to as the electromechanical coupling factor. There are many variables that affect coupling factor, including frequency. In theory, it can be advantageous to operate an ultrasonic transducer (sometimes referred to as UST) by keeping the operating frequency in the resonant frequency (Fr) or anti-resonance frequency (Fa) region. At Fr, the electrical power factor is 1, while near or approaching Fr the power factor only approaches 1. However, due to the related, very unique impedance-frequency characteristics of transducers, which can vary from transducer to transducer, drive circuit design is very difficult. In previously designed ultrasonic drivers, Phase Loop Lock (PLL) techniques were widely used. Because of the nature of analog performance, keeping a highly accurate and stable frequency output was very difficult. In theory, an ultrasonic transducer that operates at Fr or Fa has a high efficiency output. In practice, operating a UST at Fr or Fa can be difficult or impossible with PLL technology. This is why most ultrasonic drivers with a PLL design only can operate in Fr or Fa regions rather than at Fr or Fa points, and the operational phase typically may be more than 50 degrees. For most systems with rapidly changing load impedance, operation at frequencies close to Fa or Fr will cause the system to be unstable. Alternatively, a system can be kept stable by setting the operation frequency lower than Fr or higher than Fa points, so long as the frequency does not drift to a resonant point. In embodiments discussed herein, however, the ultrasonic driver can be monitored and controlled to operate at or very near Fr, a significant advantage over conventional systems.

In embodiments, Fr and Fa can be equated or analogized with serial and parallel, respectively, resonance frequencies. This is shown in Table 1:

TABLE 1

| | V/I Phase = 0 degrees | |
|---|---|---|
| Defined | Impedance = Minimum | Impedance = Maximum |
| Mechanical | Resonance frequency (Fr) | Anti-resonance frequency (Fa) |
| Electrical | Serial resonance frequency V/I phase = 0 degrees | Parallel resonance frequency V/I phase = 0 degrees |
| Ultrasound system 10 | ZFr = minimum and Phase = 0 degrees Frequency = 39 kHz~41 kHz | |

Ultrasonic transducer 70 is operated at relatively large displacements and a low load variation, thereby reducing loading effects and electrical impedance. Accordingly, ultrasonic medical applications can use a constant current control algorithm to achieve one or more of the following performance advantages: increased electrical safety due to lower operating voltage; lower operating voltage by running at Fr; proportional current to maximum tip velocity (displacement if frequency is held constant); tip displacement proportional to current; and the capability to limit excessive power surges by setting the voltage rail to an appropriate value, among others.

Generator unit 30 includes a power entry module and AC/DC power supply 300 as well as an ultrasonic driver 60. Delivery pump 50 is mounted on generator unit 30 and is controlled by a pump driver located on ultrasonic driver 60. Communications ports 302, 304, and 306 are also located on the generator unit 30, though the number and arrangement of communications ports can vary from those depicted. For example, in other embodiments more or fewer ports are provided, and one or more of the ports can comprise a wireless communications port (e.g., infrared, RF, BLUETOOTH, WIFI or some other wireless technology). These ports provide an information exchange between generator unit 30 and treatment wand 40 as well as information exchange between device 20 and user.

With respect to the Power Entry Module & AC/DC Power Input, in some embodiments the local AC MAINS is connected to an appliance inlet with a hospital grade detachable power cord. In some embodiments, different types of power cords can be used: 15 A with a 125V rate, or 10 A with a 250V rate. In some embodiments, the appliance inlet is a power entry module listed for medical applications with an 10 A current rating, 120/250 VAC voltage input, MAINS switch, integral fuse holder (2¼×1¼"/5×20 mm fuses), EMC line filter for medical applications, and is mounted on the rear panel of the chassis. Although not depicted in the figures, embodiments are contemplated that use battery power as the power source in the system's design. The battery would be located within generator 30 in various embodiments. Battery power is made possible due to the extremely efficient design discussed herein.

In some embodiments, system 10 can have a universal AC power input capability accepting a range of power input from 90V to 265 VAC. The local AC MAINS are connected to an appliance inlet component (IEC 320 C14) with a hospital grade detachable power cord. The appliance inlet is a power entry module listed for medical applications with an 115V/230V voltage input, MAINS switch, integral fuse holder (2-5×20 mm fuses), and an EMC line filter for medical applications that is mounted on the rear panel of the chassis. The MAINS switch output is connected to two AC/DC switching power modules. The two AC/DC (24V output) switching power supply modules provide +/−24V power to class-AB type amplifier use. All DC power sources +5V, +4.5V, −4.5V and 3.3V can be generated from a +24 VDC power source via DC/DC converter. The +5 VDC will provide 5V power to treatment wand 40 through the detached cable and medical grade connector 90. While class-AB amplifiers are mentioned in examples here and elsewhere, in embodiments class-D or other amplifiers also can be used.

In some embodiments, two identical AC/DC (24V output) switching power supply modules are serially connected together to provide +/−24V power to class-AB type amplifier use. The power supply can be medical grade, Class II, BF rated with 45 W output with conventional cooling. A dual color (Red/Green) LED 308 can be mounted at the front of generator unit 30. The green color indicates normal power on without errors, and the red color indicates a system error or failure. Error detail information can also display on the interface display screen 206 of treatment wand 40.

In some embodiments, there is a plurality of, such as three, communication ports in the on generator 30. The first port is a communication port 302 (such as one compatible with RS485, RS422 and/or other protocols), with 5V power and UST outputs. This port 302 is connected to treatment wand 40 through cable 90. Port 302 can be configured for full duplex communications in both directions at the same time. This port 302 can handle information exchange between generator unit 30 and treatment wand 40. In operation, both sets of microcontrollers 200 and 316 can check each other to ensure none has failed to operate through this port 302. The second port can be a USB-2 type A port, referred to herein as port 304. It can be designed for user download of information stored at the memory 310, which can comprise EEPROM, serial flash, internal non-volatile, or other suitable memory, by using a flash key or other device. This port 304 can be used for uploading software from flash key device. A third port can be an RS232-3.3V serial port, referred to herein as port 306. Port 306 can be designed for use with a PC, so the PC can communicate to the system 10 for download, upload, system debug and calibration. Also included in generator unit 30 and connected to the microcontroller are RTC at numeral 305, an audible signal generator 307 and generator temperature sensor 309, though in embodiments one or more of these features can be omitted or relocated. For example, in one embodiment audible signal generator 307 can be located in treatment wand 40 instead of or in addition to being in generator unit 30.

A microcontroller controlled pump delivery system 312 can be used for fluid delivery. Delivery system 312 comprises a pump 50 and pump driver with controls 314 for pump speed and pump door monitoring and can deliver fluid, such as saline, through a tube 120 and applicator 80 to the tip of ultrasonic transducer 70. Microcontroller (MCU1) 316 of generator unit 30 can control peristaltic pump speed to control saline flow rate for a fixed tubing size. Pump delivery system 312 generally operates at constant flow rate for all operating conditions. A cooling fan 317 is mounted in the back of generator unit 30. It is controlled by microcontroller 316 of ultrasonic driver 60.

Ultrasonic driver 60 includes a microprocessor 316 that controls, measures and monitors the drive electronics and communicates with the hardware and software of the treatment wand 40. In some embodiments, ultrasonic driver 60 includes a microprocessor 316 (such as Microchip Technology Inc. PIC32) with an 80 MHz clock and 1.56 DMIPS/MHz performance, though some other suitable microprocessor can be used in other embodiments. The drive electronics contain a digital frequency generator (DDS) 318, AC amplifier 320 and voltage and current peak detection circuits 322 and 324. Digital frequency generator 318 generates accurate frequencies set by microprocessor 316 to AC amplifier 320 that are output to ultrasonic transducer 70. In some embodiments, AC amplifier 320 can be coupled to impedance matching circuitry 326, though in other embodiments this circuitry 326 can be omitted or implemented in software or firmware rather than hardware. Voltage and current peak detection circuits 322 and 324 continually monitor the signal peaks with phase difference sensed at 328. In some embodiments, internal or external timers can be used to monitor phase difference or in the monitoring of phase difference. In operation, microprocessor 316 can adjust the digital frequency generator output frequency based on voltage vs. current phase angle so that the frequency is locked at the resonance frequency Fr of ultrasonic transducer 70. The resonance frequency Fr is not a fixed frequency, however, as it can drift with temperature and other changes. This is discussed herein below in additional detail.

Ultrasonic driver 60 includes a digital frequency generator 318, a resonance frequency control loop 400, and an output current control loop 500. Microcontroller 316 can be of sufficiently high speed so as to handle all input measurements and output settings, especially for phase comparison of cycle by cycle frequency adjustment in real time. Ultrasonic driver 60 generates electrical output with an ultrasonic frequency and a required power.

At Fr and Fa, the impedance phase is 0 degrees, which means that ultrasonic transducer 70 can achieve the highest power efficiency at those points. Accordingly, it is recognized that keeping the output frequency close to Fr or Fa would be desirable, if possible. However, it is very difficult for any control systems to operate at Fr and Fa, as at those points any small increase or decrease of frequency will cause a large impedance increase or decrease. Accordingly, most ultrasonic drivers either operate at frequencies higher than Fa or lower than Fr because frequencies are relatively stable when they are farther from Fr or Fa.

For example, some conventional systems have been designed to operate in the Fa region. These designs were relatively stable and delivered effective treatment, but output power efficiency was very low and a very high operating voltage was required. Accordingly, in order to meet regulatory safety requirements, wires with high isolation and earth protection were required, adding cost and restricted user ergonomics due to a stiffer and heavier cable.

An example comparing the voltage required by a past device operating at Fa compared to an embodiment of the currently disclosed system, operating at Fr, is set forth below:

A conventional ultrasonic transducer was operated at, or above, anti-resonance, which is approximately 1 KΩ~8 KΩ impedance. To deliver the required power to the transducer the driver must output very high voltage (300V) to the transducer. The power calculation is:

$$P = I^2 Z * \cos \varphi \quad \text{Equation 1}$$

P: input power of transducer
I: input current
Z: transducer impedance in Ohm
φ: voltage vs. current phase angle (−90°~+90°)
If the transducer requires 7 W power, φ=85°, Z=1500Ω, from Equation 1 the current will be:

$$I = \sqrt[2]{\frac{P}{Z * \cos \varphi}} = \sqrt[2]{\frac{7\,W}{1500\Omega * \cos(85°)}} = 230\,mA$$

Accordingly, a power supply voltage would be: (230 mA*1500Ω)=345V.

An embodiment of system 10, in contrast, operates at Fr with constant current output control. Its impedance is about 25~80Ω and voltage vs. current phase angle close to 0 degrees. The power efficiency is almost 100%. An example with Fr impedance is 50Ω.

If the transducer requires 7 W power, φ=0°, Z=50Ω, the current will be:

$$I = \sqrt[2]{\frac{P}{Z * \cos \varphi}} = \sqrt[2]{\frac{7\,W}{50\Omega * \cos(0°)}} = 370\,mA$$

and the power supply voltage will be: 370 mA*50Ω=18.7V

Accordingly, embodiments of system 10, with a low voltage operation condition, can be much more efficient and safer than conventional designs. Any voltage surges resulting when transducer impedance is increased can be limited by setting the voltage rail to an appropriate value.

Microcontroller 316 of the ultrasonic driver controls all input and output functions and performs all control loops, calculations. Embodiments of microcontroller 316 can include one or more of the following: a 80 MHz maximum frequency; 1.56 DMIPS/MHz (Dhrystone 2.1) performance; an operating voltage range of 2.3V to 3.6V; a 512K flash memory (plus an additional 12 KB of Boot Flash); a 128K SRAM memory; USB 2.0-compliant full-speed device and On-The-Go (OTG) controller; up to 16-channel, 10-bit Analog-to-Digital Converter; six UART modules with RS-232, RS-485 and LIN support; and up to four SPI modules. These characteristics are merely examples and can vary in other embodiments.

The ultrasonic frequency generator is a digital frequency generator 318 that provides numerous advantages over conventional designs. In some conventional designs, PLL technology was used with or comprises part of a voltage control oscillator (VCO) for generating a fixed ultrasonic frequency. However, this produced an output frequency that is low resolution and not flexible for wide frequency range applications without hardware changes. Further, the frequency stability was imprecise since the VCO is affected by temperature, noise and power ripple.

In the current ultrasonic therapy system 10, a Direct Digital Synthesis programmable frequency generator (DDS) is used as part of the frequency generator 318. Because a DDS is digitally programmable, the output frequency can be easily adjusted over a wide range. DDS permits simple adjustments of frequency in real time to locate resonance frequencies or compensate for temperature drift. The output frequency can be monitored and adjusted based on phase difference measurements in embodiments, and can be continually adjusted by microcontroller 316 at real time speed. Advantages of using DDS to generate frequency include: digitally controlled sub-Hertz frequency-tuning resulting in sub-degree phase-tuning capability; extremely fast speed in tuning output frequency (or phase); and phase-continuous frequency hops with no overshoot/undershoot or analog-related loop setting-time anomalies, among others. In embodiments, a sine-wave output can be generated by the ultrasonic transducer, which can provide cleaner signals to sensing circuitry. Additionally, because the voltage and current maintain a very close semblance of a sine wave, peak sensing can be used without requiring more elaborate true Root Mean Square (RMS) conversion.

Figure 5:
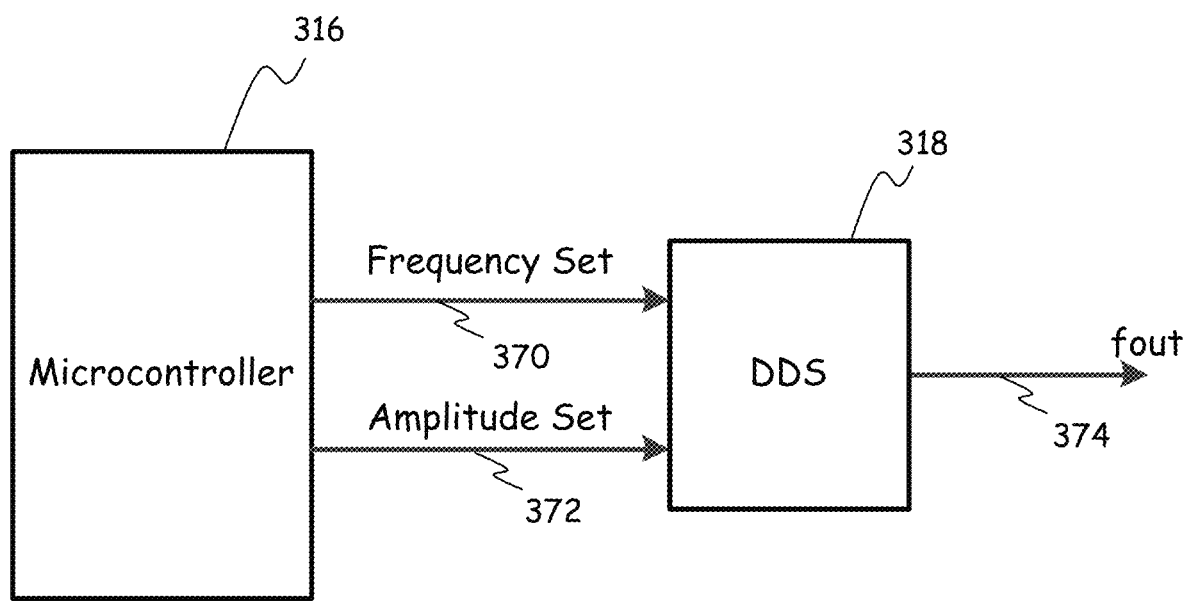
FIG. 5 is a diagram of the interaction of the DDS (Direct Digital Synthesis) feature and microprocessor that provides digital frequency generation, according to an embodiment.

The digital architecture of DDS eliminates the need for the manual tuning and tweaking related to components aging and temperature drift in analog synthesizer solutions, and the digital control interface of the DDS architecture facilitates an environment where systems can be remotely controlled and optimized with high resolution under processor control. FIG. 5 shows the system's digital frequency generation using microcontroller 316 and DDS 318. Specifically, frequency set 370 and amplitude set 372 are received by DDS 318 which generates an output frequency 374 ($f_{out}$).

Figure 6:
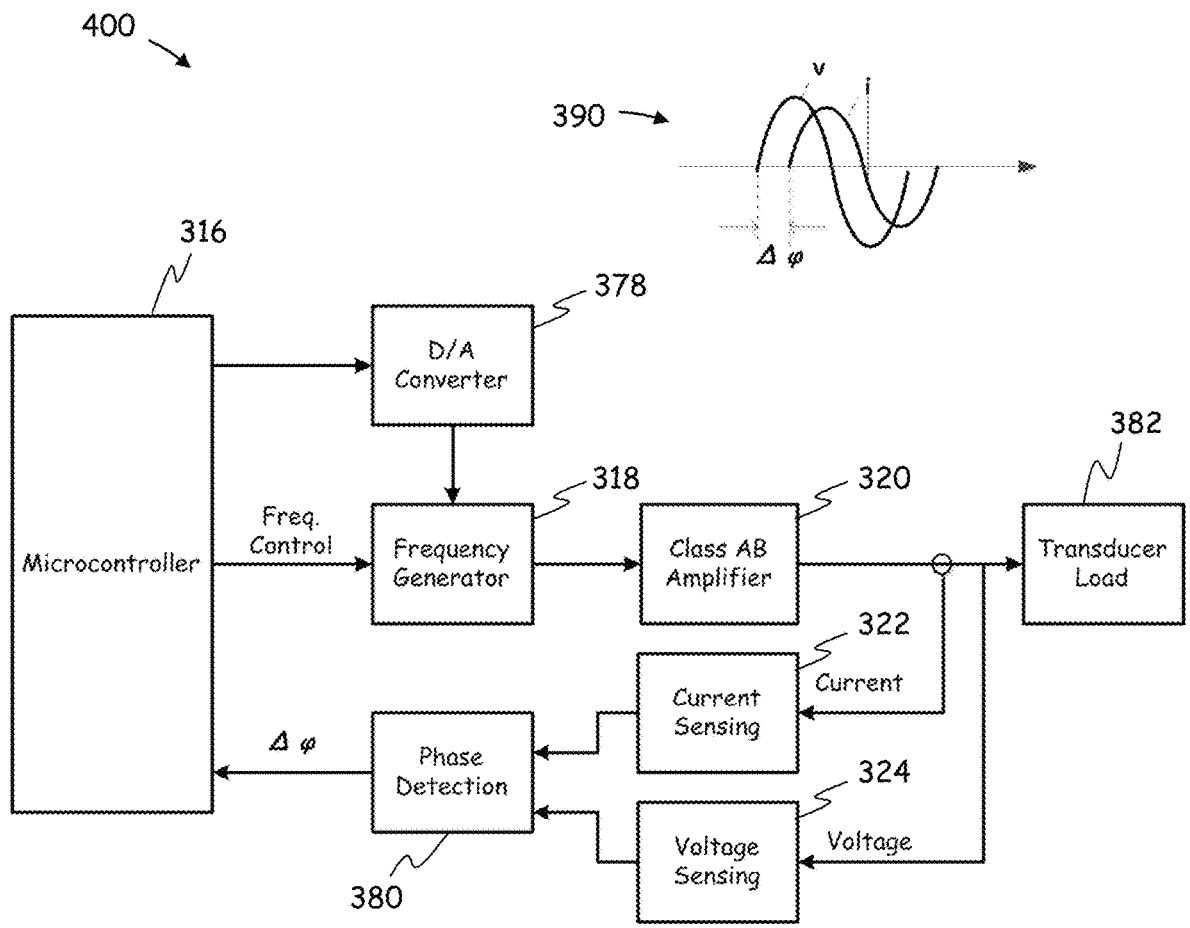
FIG. 6 is a diagram of the frequency control loop of the system, according to an embodiment.

FIG. 6 sets forth the frequency control loop 400 for system 10. Frequency control loop 400 includes a digital frequency generator (DDS) 318, D/A converter 378, phase detector 380 and microprocessor 316. The drive electronics utilize the digital frequency generator 318, AC amplifier 320 and voltage and current peak detection circuits 322 and 324. Digital frequency generator 318 generates a high accuracy and precision frequency signal, set by the microprocessor 316, to AC amplifier 320 that outputs across a transducer load 382 to ultrasonic transducer 70. At start-up, system 10 performs a Power On Self-Test (POST) and communicates with ultrasonic transducer 70 to gather information on characteristics of ultrasonic transducer 70 and determine that treatment wand 40 is functioning properly.

Specifically, when initially energized, microprocessor 316 can be programmed to perform a frequency sweep using a sine wave to determine the resonant frequency by evaluating and looking for a relative minimum impedance of ultrasonic transducer 70. The sweep is confined to a smaller defined interval based on the information embedded in treatment wand 40 regarding the operating characteristics of ultrasonic transducer 70. This includes the information stored about ultrasonic transducer 70 at the time of manufacture or otherwise programmed or updated. During the system start, digital frequency generator 318 can scan frequencies from a start frequency (min 20 KHz, adjustable) to an end frequency (max 50 KHz, adjustable) to find the resonance frequency (Fr). Microprocessor 316 can adjust the digital frequency generator output frequency based on voltage vs. current phase angle so that the frequency lockup is maintained at the resonance frequency of ultrasonic transducer 70 (i.e., at a 0° phase angle). Because the frequencies continually shift due to temperature change and other factors, the phase of output voltage and current will change as well. The voltage vs. current phase detection circuits are continually monitored for the phase difference and the frequency adjusted accordingly. Resonance frequency is not a fixed frequency. This is due to heating and other factors causing a slight drift change with temperature. Specifically, increased temperature can cause decreased resonant frequency.

In order to keep output frequency lockup at resonance frequency, frequency control loop 400 can monitoring output voltage vs. current phase angle in real time and continually adjust operating frequency to match the current resonance frequency. In some embodiments, microprocessor 316 can maintain $\Delta\varphi$ (as illustrated at 390) to less than about 0.1 degree inaccuracy and provide sufficient capabilities to achieve accuracy of about 0.1 Hz or better. In some embodiments, resonance frequency is digitally controlled to better than about 0.5 Hz while maintaining constant energy output.

Figure 7:
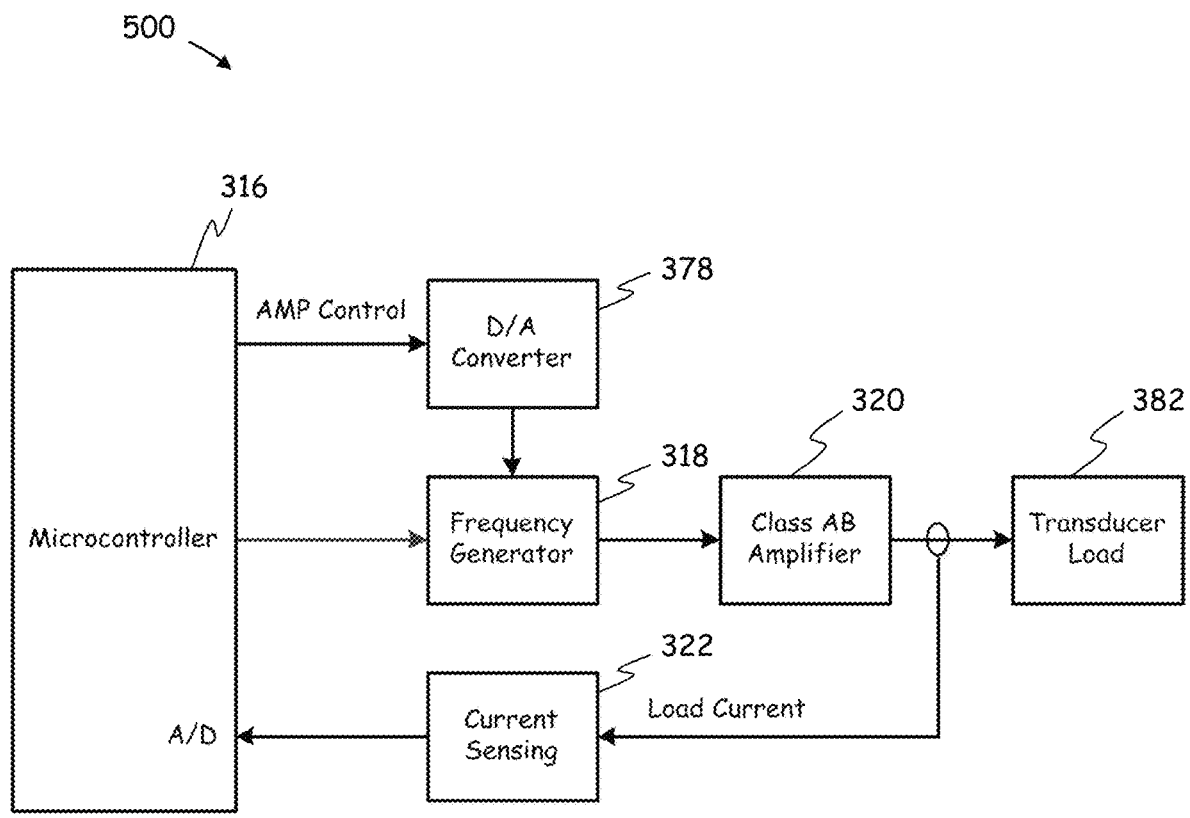
FIG. 7 is a diagram of the constant current control loop of the system, according to an embodiment.

FIG. 7 sets forth output current control loop 500 for system 10. Output current control loop 500 is designed to provide a constant current output. Since the transducer output displacement is a function of transducer drive current, the control output current (not voltage) will control output displacement. Displacement, of a given tip area, determines the amount of ultrasound energy delivered/output. Microprocessor 316 monitors the output current via a sensing resistor then adjusts the digital frequency generator 318 output signal level to maintain constant current output thus maintaining a constant output displacement from the tip of the horn. Current sensing circuit 322 can sense peak current, and in some embodiments, such as for data logging format output or other purposes, convert peak value to an RMS value. Any waveform distortion can cause converter errors, causing current control errors and ultimately displacement errors. To avoid this situation, embodiments of the system can use RMS sensing technology to reduce the errors. This can be implemented if the waveform has considerable distortion, for example.

In system 10, the digital frequency generator 318 can be used to allow for selection and use of different frequencies via software implementation. Configurations having operating frequencies ranging from about 20 kHz to about 50 kHz are possible. Digital frequency generator 318 is digitally programmable. Accordingly, the phase and frequency of a waveform can be easily adjusted without the need to change hardware (frequency generating components), unlike VCO or PLL based generators, as would normally be required to change when using traditional analog-programmed waveform generators. Digital frequency generator 318 permits simple adjustments of frequency in real time to locate resonance frequencies or compensate for temperature drift or other deviations in the resonant frequency. The output frequency can be monitored via phase difference measurements and continually adjusted by microcontroller 316 at real time speed.

There are many advantages to using digital frequency generator 318 to generate frequency. For example, this provides a digitally controlled, 0.01-Hertz frequency-tuning and sub-degree phase-tuning capability as well as extremely fast speed in tuning output frequency (or phase). The digital frequency generator 318 also provides phase-continuous frequency change with no overshoot/undershoot or analog-related loop setting-time anomalies. The digital architecture of the digital frequency generator 318 eliminates the need for the manual tuning and tweaking related to components aging and temperature drift in analog synthesizer solutions, and the digital control interface of the digital frequency generator architecture facilitates an environment where systems can be remotely controlled and optimized with high resolution under processor control.

In this system, ultrasonic driver 60 outputs a sine waveform through a class AB power amplifier 320. It can operate at frequency from 20 KHz to 50 KHz, constant current mode. The ultrasonic driver 60 outputs current from 0 to 0.65 A, voltage from 0 to 30 Vrms, Max power to 19.5 W, in embodiments, though these values and ranges can vary in other embodiments. The ultrasonic driver output can scan resonance frequencies from the 20 KHz to 50 KHz range, detect minimum impedance (0° degree phase angle of voltage vs. current), and then lock operational frequency to resonance frequency of the ultrasonic transducer 70 at a ±0.5 Hz accuracy level. Parameters may vary in various embodiments. In certain embodiments, the drive voltage requirements are less than 50 Vrms for the system.

The technology of system 10 is unique in that it sees an essentially constant load. The no-load condition is similar to the operational load. Being a non-contact treatment and dispensing only a small amount of fluid onto the horn does not create a significant variation in the load/output, allowing the system to be run at resonance (Fr). Running and controlling the system at Fr allows improved efficiency, as previously discussed. Typical ultrasound applications such as welding, mixing, cutting, and cleaning have significant variation in the load, e.g., going from a no-load to full load condition. The variation makes control of the output very difficult and requires greater power at the cost of efficiency.

Figure 8:
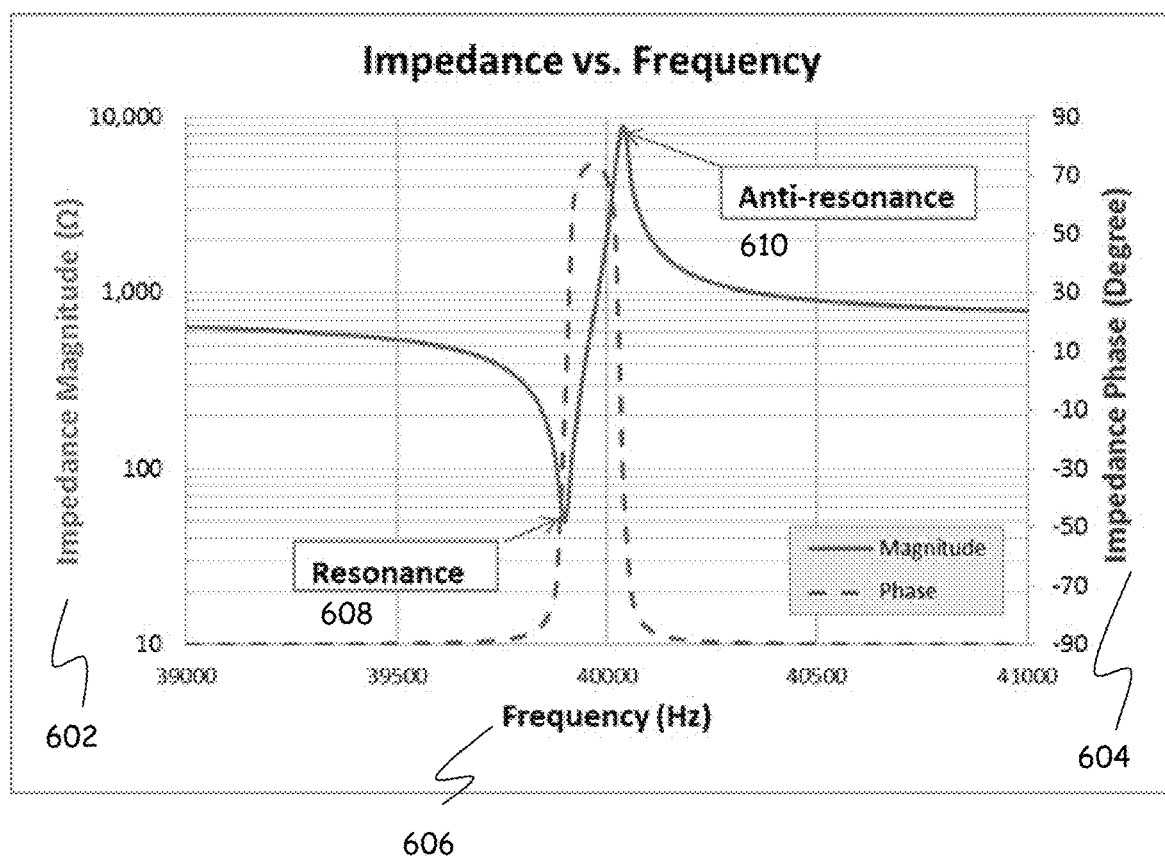
FIG. 8 is a graph of an example of impedance versus frequency, in an ultrasonic transducer device, according to an embodiment.

FIG. 8 is a graph that helps to illustrate advantages of using system 10's ultrasonic driver based on the impedance and frequency characteristics of ultrasonic transducer 70. Specifically, the dramatic change in impedance magnitude 602 and phase 604 is seen for changes in frequency 606 for even small deviations from the resonance frequency 608 and anti-resonance frequency 610. Ultrasonic transducer 70 is a component that converts electrical energy to mechanical energy. Its impedance and frequency characteristics create significant drive circuit design challenges, especially if trying to optimize for low power input and accuracy. Traditional ultrasonic driver designs typically use Phase Loop Lock (PLL) frequency control technology. However, analog system performance generally does not allow for accuracy and stable frequency output. Accordingly, this can make it difficult to control the system precisely with analog systems. In theory, an ultrasonic transducer operating at resonance frequency Fr or anti-resonance Fa frequency has a high efficiency output. In practice, when ultrasonic transducers operate at resonance frequency or anti-resonance frequency, it is almost impossible using PLL technology to maintain elegant control. Typical ultrasonic drivers utilize an analog PLL based design for control. The PLL based designs operate close to resonance frequency or anti-resonance frequency points, but due to their inherent inaccuracy, these often operate at some phase angle away from Fr or Fa leading to inefficiencies.

In system 10, a constant current control algorithm can be used. It can operate at resonance frequency, rather than just close to resonant frequency. The difference between anti-resonance and resonance is that at anti-resonance the system can operate with high impedance and at resonance with lowest impedance. The high impedance can be in the range of about 5 KΩ to about 50 KΩ, and low impedance can be in a range of about 20Ω to about 100Ω in certain embodiments, for example.

Since ultrasonic transducer 70 is operated with relatively large displacements and a low load variation, there is a significant reduction in loading effects and electrical impedance variation. Many ultrasonic medical applications use a constant current control algorithm because of the following performance advantages: electrical safety (such as due to a lower operating voltage); current that is proportional to frequency and/or maximum tip velocity (displacement if frequency is held constant); fewer excessive power surges (by setting and maintaining the voltage rail to an appropriate value); and the ability to monitor and control displacement of the tip.

Some embodiments of system 10 have three modes of operation: a TREATMENT mode; an INFORMATION mode; and a TERMINAL mode. If the user enters the TREATMENT or normal operating mode upon power up, the user can select the length of time for a treatment and energize the acoustic output to treat a patient. If the INFORMATION mode is entered on power up with a flash key plug to the USB port, user information can be downloaded that has been stored in the memory to flash or new software can be uploaded from the flash key to the system. Finally, a TERMINAL mode can be selected that is an engineering mode for internal device calibration, system characterization, and system evaluation.

System 10 may also save all information of the device hardware and software as well as the user's input and treatments during operation. In some embodiments, system 10 has enough memory storage for all information saved for at least one year of operation. For example, system 10 may implement 2 MB EEPROM and flexible size memory in some embodiments.

FIGS. 9a-g combine to provide a flow diagram operational method 700 of ultrasonic system 10. In various embodiments, one or more tasks or steps can be omitted, or intervening tasks or steps can be carried out in addition those specifically depicted. Operation begins by first powering on the system at 702, followed by conducting a system self-test at 704.

Figure 9A:
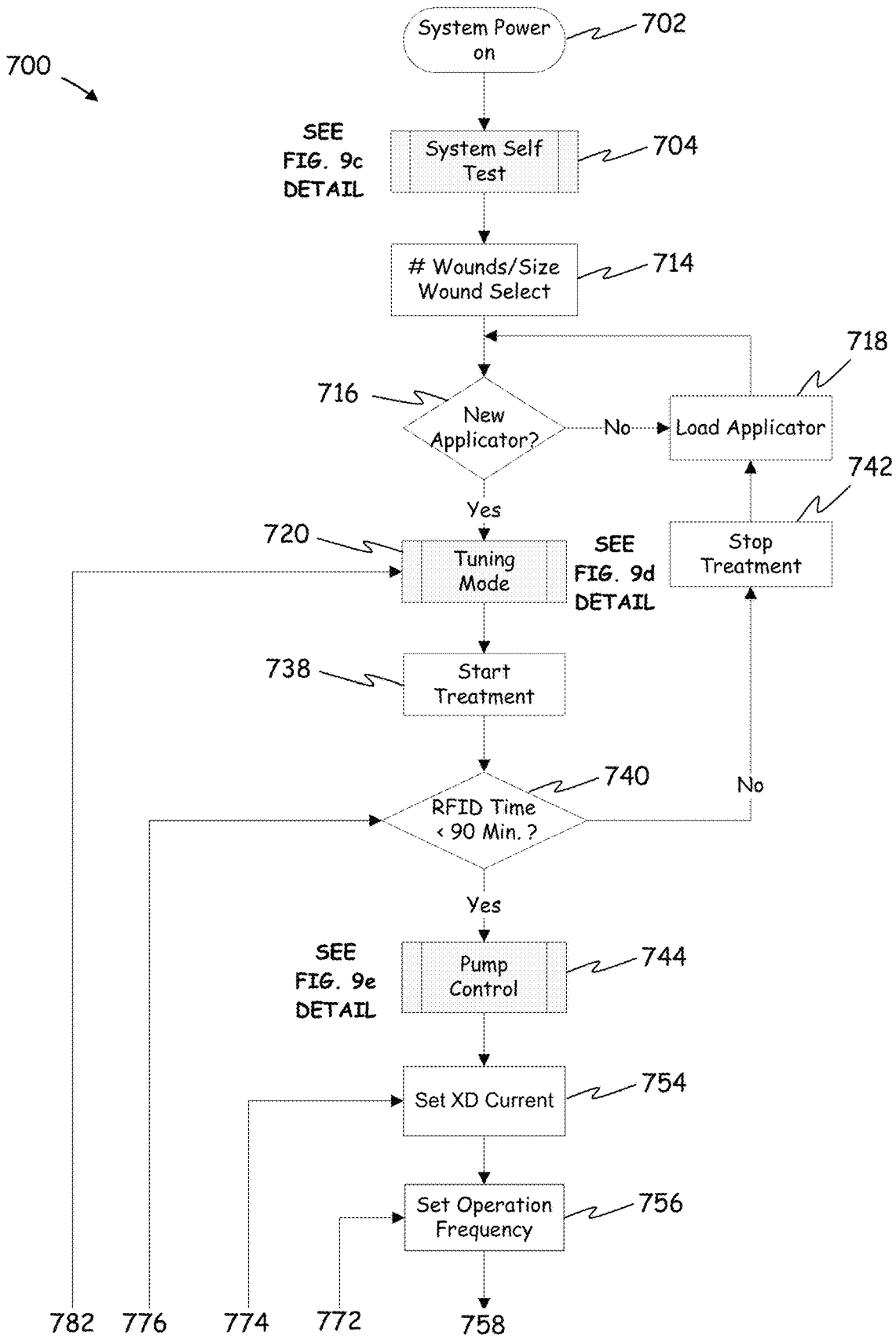
FIGS. 9a-9g show a diagram of the operation of the ultrasonic therapy system, according to an embodiment.
Figure 9B:
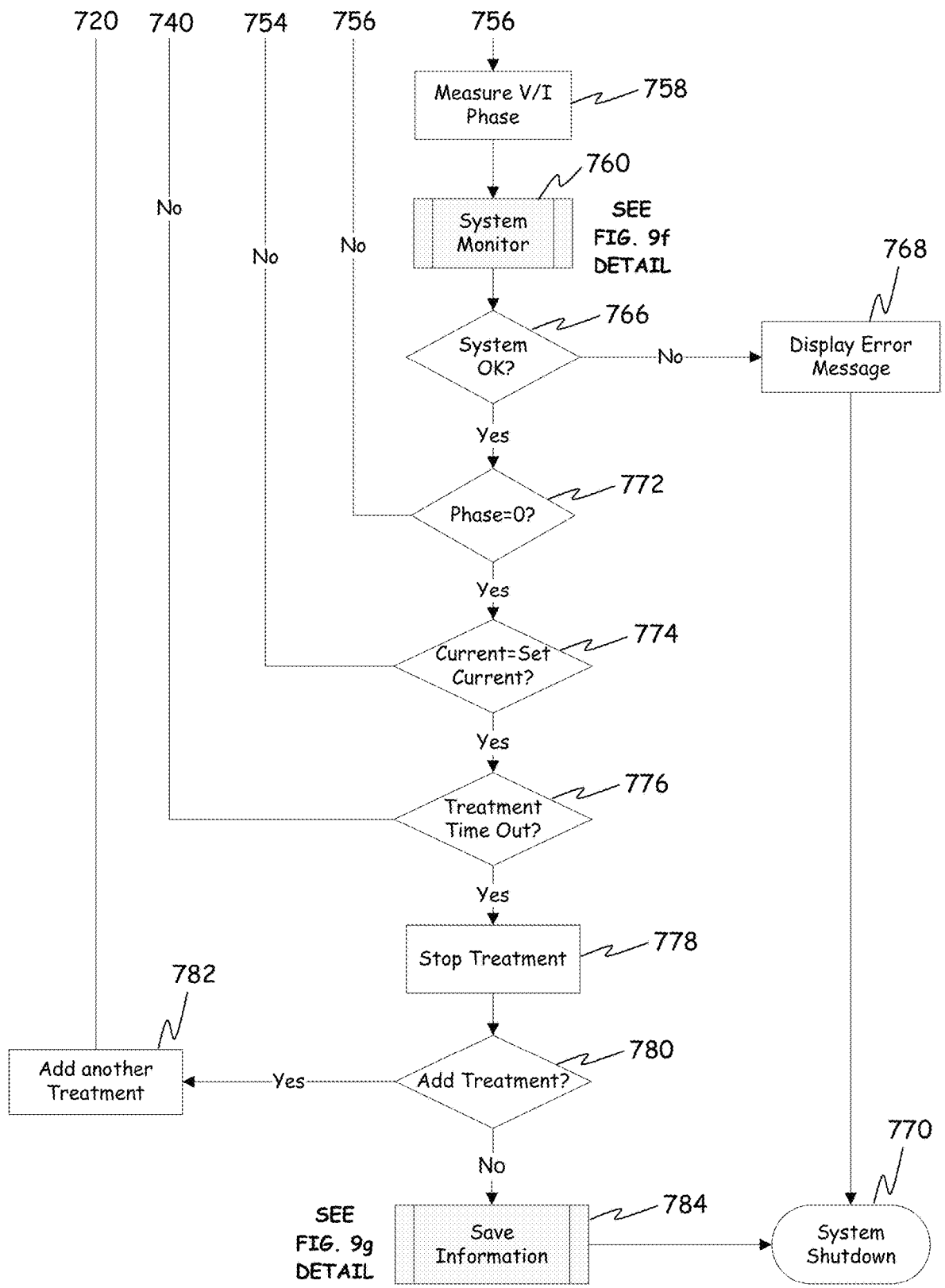
Figures 9C, 9D:
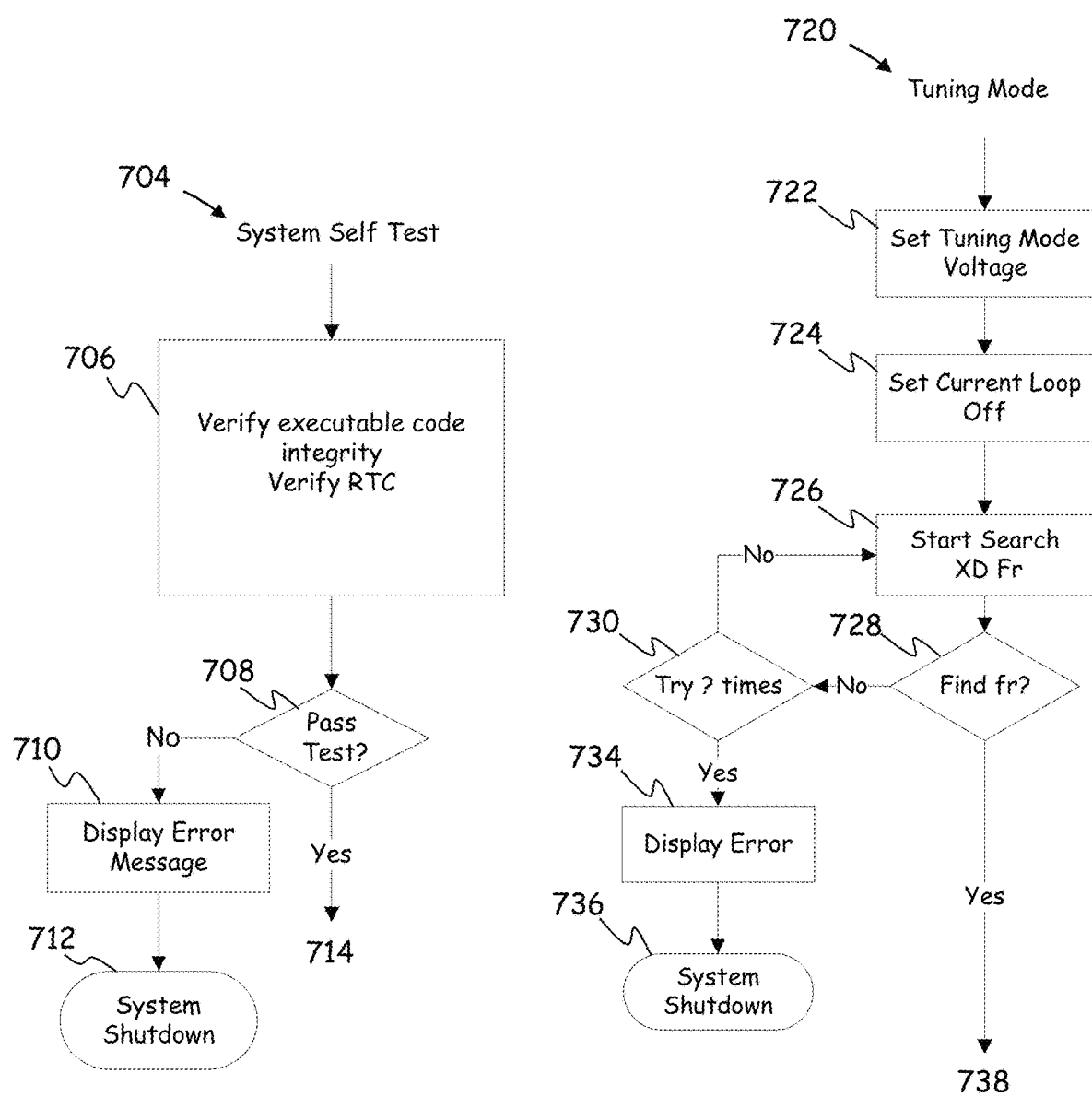

FIG. 9c shows the steps of self-test 704. First, system 10 can verify the integrity of the executable code and verifies RTC at 706. Next, at 708, if the self-test is passed, operation continues on to 714. If the self-test is not passed, an error message is displayed at 710 on display 206 and the system may be shut down at 712. The error message may be used to communicate the issue to customer service.

If 714 is reached (in FIG. 9a), the number of wounds and size of wounds are input. If a new applicator 80 is present at 716, operation proceeds, if not, a new applicator 80 is loaded at 718. Next, at 720, tuning mode commences.

FIG. 9d shows tuning mode 720. First, the tuning mode voltage is set at 722. Next the current loop is set off at 724, followed by a search for the resonance frequency Fr of ultrasonic transducer 70 at 726. If the resonance frequency is found at 728, the system continues on to 738. If the resonance frequency is not found the system will try again for a set number of times at 730. If resonance frequency is not found, after these attempts, an error is displayed on the system display 206 at 734, followed by system shutdown at 736.

If 720 is reached (in FIG. 9a), treatment is started following a successful tuning mode. Next, at 740, the system checks the RFID tag on the applicator 80 for a valid state and to ensure that the treatment has proceeded for less than ninety minutes. If not, treatment is stopped at 742 and a new applicator is loaded at 718 before reengaging the operation at 716. If the RFID tag indicates treatment of less than 90 minutes and a valid state at 740, then operation continues on to pump control at 744.

Figures 9E, 9F:
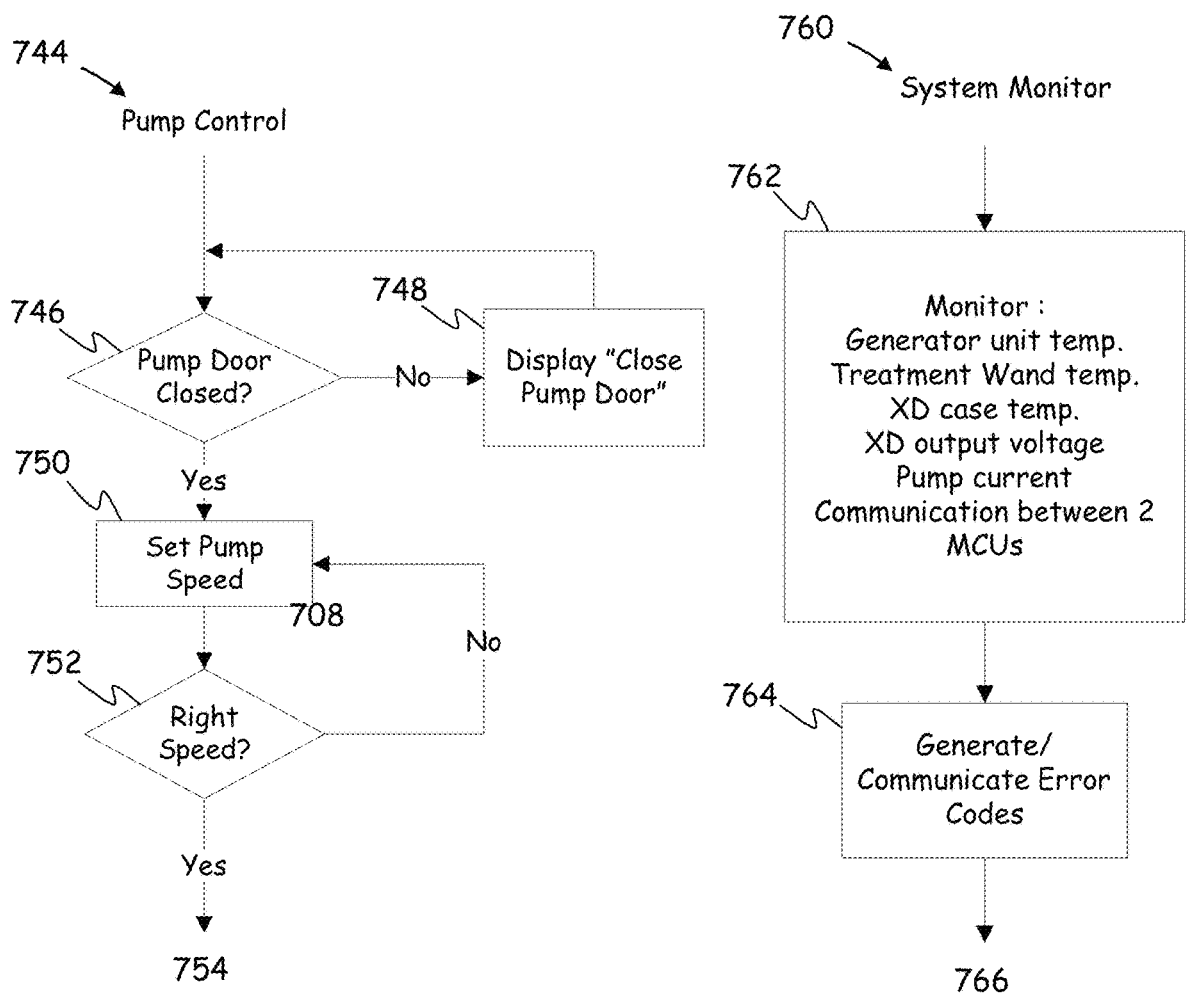

FIG. 9e shows the pump control 744. First, the system 10 can check that the pump door of the peristaltic pump 50 located on the exterior of the console/generator unit 50 is closed at 746. If not, the display 206 indicates a message to close the pump door at 748. If the pump door is closed, operation continues to 750 where the pump speed is set. The system then can check the pump speed at 752, and the pump speed is set again if necessary, before proceeding on to 754 when the pump control is complete. In some embodiments, checking pump speed and setting or resetting the speed (e.g., one or both of 750, 752) can be omitted.

When 754 is reached (FIG. 9a), the current is set for the ultrasonic transducer 70. Next, the operation frequency is set at 756 and the voltage and current phase is measured at 758. See FIG. 9b. Next, monitoring the system commences at 760.

FIG. 9f shows monitoring the system at 760. First the system monitors: the temperature of the generator unit 30; the temperature of the treatment wand 40; the temperature of the case of the ultrasonic transducer 70; the output voltage of the ultrasonic transducer 70; the current of the pump 50; and the communication between the two microprocessors 200 and 316 (MCU2 and MCU1). Next, error codes are generated and communicated at 764 before returning to 766.

When 766 is reached (FIG. 9b), if the system is not determined to be in order, an error message is communicated on the display 206 at 768 and the system is shut down at 770. If, however, the system is determined to be ok at 766, the system checks to ensure the voltage/current phase angle is 0° at 774. If not, operation reverts to 756 in which the operation frequency is adjusted to so that a voltage/current phase angle of 0° can be achieved. If voltage/current phase angle is set to 0° at 772, the system checks to ensure the current sensed is equivalent to the current that was set for the system at 774. If the current does not match, operation reverts to 754 and the transducer sets the current again before continuing. If the current is appropriate at 774, the system then tests to see if the treatment has timed out at 776. If it has not timed out, operation reverts to 740 and the test of 90 minute RFID time limit is conducted. If treatment has timed out at 776, the treatment is stopped at 778 followed by the option to add a further treatment or additional time at 780. If another treatment or additional time is desired, another treatment is added at 782 and operation reverts to the tuning mode at 720. If no further treatment is desired, information is saved at 784.

Figure 9G:
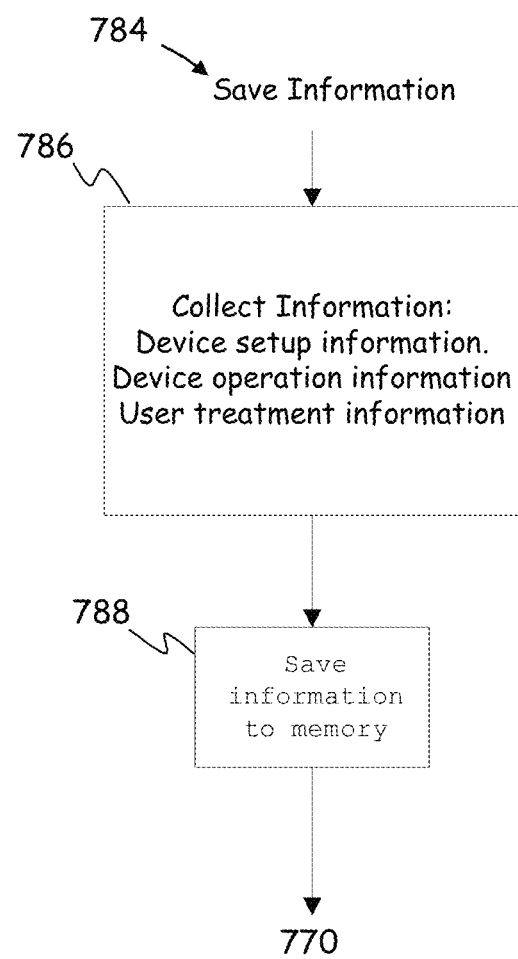

FIG. 9g shows saving information 784 in greater detail. First, the system collects device setup information, device operation information, and user treatment information at 786. Next, at 788, information is saved to memory (which can be EEPROM or some other memory type or form, such as serial flash or non-volatile in various embodiments) before continuing to system shutdown at 770.

As understood by the various system checks and protocols in this operational explanation, the operation of the system can be suspended at many points. Advantageously, in certain embodiments, both microprocessor 200 and microprocessor 316 are configured to individually suspend operation of the ultrasonic system in fault condition situations. This arrangement provides enhanced safety not present in other types of designs.

It should also be appreciated that the exemplary embodiment or exemplary embodiments are only examples, and are not intended to limit the scope, applicability, or configuration of the invention in any way. Rather, the foregoing detailed description will provide those skilled in the art with an enabling disclosure for implementing the exemplary embodiment or exemplary embodiments. It should be understood that various changes can be made in the function and arrangement of elements without departing from the scope of the invention as set forth in the appended claims and the legal equivalents thereof.

The embodiments above are intended to be illustrative and not limiting. Additional embodiments are within the claims. Although the present invention has been described with reference to particular embodiments, workers skilled in the art will recognize that changes may be made in form and detail without departing from the spirit and scope of the invention.

Various modifications to the invention may be apparent to one of skill in the art upon reading this disclosure. For example, persons of ordinary skill in the relevant art will recognize that the various features described for the different embodiments of the invention can be suitably combined, un-combined, and re-combined with other features, alone, or in different combinations, within the spirit of the invention. Likewise, the various features described above should all be regarded as example embodiments, rather than limitations to the scope or spirit of the invention. Therefore, the above is not contemplated to limit the scope of the present invention.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:

1. A method for digitally generating and controlling a low frequency ultrasound used in a non-contact medical ultrasound therapy system, comprising:
performing a power on self-test to an ultrasonic therapy system that includes a treatment wand comprising an ultrasonic transducer and a generator comprising an ultrasonic driver;
performing a frequency sweep using a sine wave to determine a serial resonance frequency of the ultrasonic transducer by identifying a relative minimum impedance of the ultrasonic transducer;
adjusting a digital frequency generator output frequency based on voltage vs. current phase angle to maintain a frequency lockup in a phase-continuous manner at the serial resonance frequency for exclusively non-contact low-load conditions and no-load conditions, wherein the system is driven at a constant current which maintains constant output displacement;
and monitoring voltage and phase detection circuits of the ultrasound therapy system for phase difference, and
wherein both a first microprocessor and a second microprocessor are configured to individually suspend operation of the ultrasound therapy system in a fault condition, wherein the fault condition corresponds to one or more of:
a temperature of the generator,
a temperature of the treatment wand,
a temperature of the ultrasonic transducer, an output voltage of the ultrasonic transducer, or a communication failure between the first microprocessor and the second microprocessor.

* * * * *